(12) United States Patent
Takenouchi et al.

(10) Patent No.: US 10,759,897 B2
(45) Date of Patent: Sep. 1, 2020

(54) URETHANE-MODIFIED (METH)ACRYLAMIDE COMPOUND AND ACTIVE ENERGY RAY CURABLE RESIN COMPOSITION CONTAINING SAME

(71) Applicant: KJ CHEMICALS CORPORATION, Tokyo (JP)

(72) Inventors: Miki Takenouchi, Kumamoto (JP); Kouji Teramoto, Kumamoto (JP); Yusuke Adachi, Kumamoto (JP)

(73) Assignee: KJ CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 15/754,160

(22) PCT Filed: Sep. 13, 2016

(86) PCT No.: PCT/JP2016/076913
§ 371 (c)(1),
(2) Date: Feb. 21, 2018

(87) PCT Pub. No.: WO2017/047565
PCT Pub. Date: Mar. 23, 2017

(65) Prior Publication Data
US 2018/0244832 A1 Aug. 30, 2018

(30) Foreign Application Priority Data

Sep. 15, 2015 (JP) .................................. 2015-181304
Sep. 2, 2016 (JP) .................................. 2016-172082

(51) Int. Cl.
| | |
|---|---|
| *C08G 18/67* | (2006.01) |
| *C08G 18/75* | (2006.01) |
| *C08G 18/40* | (2006.01) |
| *C08G 18/78* | (2006.01) |
| *C08G 18/76* | (2006.01) |

(Continued)

(52) U.S. Cl.
CPC .......... *C08G 18/678* (2013.01); *A61K 8/8164* (2013.01); *A61Q 3/02* (2013.01); *C08G 18/3212* (2013.01); *C08G 18/4018* (2013.01); *C08G 18/4211* (2013.01); *C08G 18/44* (2013.01); *C08G 18/48* (2013.01); *C08G 18/4825* (2013.01); *C08G 18/4854* (2013.01); *C08G 18/61* (2013.01); *C08G 18/6607* (2013.01); *C08G 18/671* (2013.01); *C08G 18/672* (2013.01); *C08G 18/69* (2013.01); *C08G 18/73* (2013.01); *C08G 18/755* (2013.01); *C08G 18/758* (2013.01); *C08G 18/7621* (2013.01); *C08G 18/7893* (2013.01); *C08G 18/792* (2013.01); *C08J 7/0427* (2020.01); *C08L 75/16* (2013.01); *C09D 4/00* (2013.01); *C09D 11/101* (2013.01); *C09D 11/107* (2013.01); *C09D 11/30* (2013.01); *C09D 175/16* (2013.01); *C09J 4/00* (2013.01); *C09K 3/10* (2013.01); *C09K 3/1018* (2013.01); *G02B 5/305* (2013.01); *C08J 2475/16* (2013.01); *C09K 2200/0627* (2013.01)

(58) Field of Classification Search
CPC ........ C08G 18/44; C08G 18/48; C08G 18/61; C08G 18/69; C08G 18/73; C08G 18/678; C08G 18/755; C08G 18/758; C08G 18/4018; C08G 18/184825; C08G 18/184854; C08G 18/7621; C08G 18/7893; C08G 18/4825; C08G 18/4854; C09J 4/00; C09D 4/00; C09D 11/30; C09D 11/101; C09D 11/107; C09K 3/10; C09K 3/1018; C09K 2200/0627; A61K 8/8164; A61Q 3/02

See application file for complete search history.

(56) References Cited

U.S. PATENT DOCUMENTS

| | | | | |
|---|---|---|---|---|
| 2014/0309360 | A1* | 10/2014 | Miyake | .................... C09D 5/02 524/553 |
| 2017/0009001 | A1* | 1/2017 | Takenouchi | ........... C08G 18/44 |
| 2018/0244831 | A1 | 8/2018 | Hirata et al. | |

FOREIGN PATENT DOCUMENTS

| | | |
|---|---|---|
| EP | 3121209 A1 | 1/2017 |
| EP | 3351575 A1 | 7/2018 |

(Continued)

OTHER PUBLICATIONS

International Search Report from Patent Application No. PCT/JP2016/076913, dated Dec. 6, 2016.

(Continued)

*Primary Examiner* — Bijan Ahvazi
(74) *Attorney, Agent, or Firm* — Greenblum & Bernstein, P.L.C.

(57) ABSTRACT

Provided is an active energy ray curable resin which has excellent compatibility with organic solvents, general purpose acrylic monomers, and oligomers, and a high curing property with an active energy ray, and also has a high adhesion property for each substrate. A cured film obtained by ultraviolet curing of the active energy ray curable resin has an excellent surface curing property, scratch resistance and bending resistance, while also having high transparency. Provided is a urethane modified (meth)acrylamide compound having a urethane bond and one or more (meth)acrylamide groups in the molecule. The urethane modified (meth)acrylamide compound has excellent compatibility with organic solvents, general purpose acrylic monomers, and oligomers, and exhibits a high curing property with an active energy ray. Also provided is an active energy ray curable resin which is obtained with the urethane modified (meth)acrylamide compound and has an excellent surface curing property, scratch resistance, and bending resistance.

20 Claims, No Drawings

(51) Int. Cl.
*A61K 8/81* (2006.01)
*C09D 11/30* (2014.01)
*C09K 3/10* (2006.01)
*C08G 18/32* (2006.01)
*C08G 18/42* (2006.01)
*C08G 18/66* (2006.01)
*C08L 75/16* (2006.01)
*C08G 18/79* (2006.01)
*C09D 175/16* (2006.01)
*G02B 5/30* (2006.01)
*C08J 7/04* (2020.01)
*A61Q 3/02* (2006.01)
*C08G 18/44* (2006.01)
*C08G 18/48* (2006.01)
*C08G 18/61* (2006.01)
*C08G 18/69* (2006.01)
*C08G 18/73* (2006.01)
*C09D 4/00* (2006.01)
*C09D 11/101* (2014.01)
*C09D 11/107* (2014.01)
*C09J 4/00* (2006.01)

(56) References Cited

FOREIGN PATENT DOCUMENTS

| | | |
|---|---|---|
| GB | 1505898 A | 3/1978 |
| JP | 2002-37849 A | 2/2002 |
| JP | 2005-281412 A | 10/2005 |
| JP | 2008-045032 A | 2/2008 |
| JP | 2009-244460 A | 10/2009 |
| JP | 2010-128417 A | 6/2010 |
| JP | 2011-218616 A | 11/2011 |
| JP | 2012-82288 A | 4/2012 |
| JP | 2013-227519 A | 11/2013 |
| JP | 2013227519 * 11/2013 | ............ C08G 18/67 |
| JP | 2015028607 A | 2/2015 |
| JP | 2015-71682 A | 4/2015 |
| JP | 2015071682 * 4/2015 | ............ C08G 18/67 |
| JP | 2016-113518 A | 6/2016 |
| WO | 2007/139157 A1 | 12/2007 |
| WO | WO-2007139157 A1 * 12/2007 | ........... C08G 18/671 |
| WO | WO-2015101364 A2 * 7/2015 | ............... A61K 8/34 |

OTHER PUBLICATIONS

Notification of Reasons for Refusal for Patent Application No. 2017-518368 dated Jul. 4, 2017.
Notification of Reasons for Refusal for Patent Application No. 2017-518368 dated Sep. 13, 2017.
Notification of Reasons for Refusal for Patent Application No. 2017-518367 dated Jul. 4, 2017.
U.S. Appl. No. 15/754,854, filed Feb. 23, 2018.
Extended European Search Report from Application No. EP 16846436.0 dated Mar. 13, 2019.
First Korean Office Action issued in Korean Patent Application No. 10-2018-7009431 dated Jul. 27, 2018.

* cited by examiner

URETHANE-MODIFIED (METH)ACRYLAMIDE COMPOUND AND ACTIVE ENERGY RAY CURABLE RESIN COMPOSITION CONTAINING SAME

TECHNICAL FIELD

The present invention relates to a urethane modified (meth)acrylamide compound which has excellent compatibility with organic solvents and general purpose acrylic monomers and oligomers, high curing rate with an active energy ray, number average molecular weight of 250 or more but less than 4,500, and (meth)acryl equivalents within the range of from 250 or more to less than 3,000. The present invention further relates to an active energy ray curable resin composition containing the urethane modified (meth)acrylamide compound, which has an excellent surface curing property, heat resistance, and scratch resistance and also a low curing shrinkage property and high transparency. The present invention still further relates to a molded article of the active energy ray curable resin composition.

BACKGROUND ART

Based on combination of polyols and polyisocyanates as raw materials, structure of a urethane resin can be designed to meet the required characteristics, including soft to hard resins. For such reasons, the urethane resin is used in a broad range of industrial fields. Furthermore, use of the active energy ray curable resin to be cured by ultraviolet ray (UV) or electron beam (EB) is widened in recent years due to the characteristics like productivity, energy saving, and low environmental load compared to a thermocurable composition and a solvent-based resin composition. Among the flows of those technological innovations, research and development of an active energy ray curable urethane acrylate, which is a urethane resin having an unsaturated group like acrylate bound to the end, in particular, research and development of application techniques thereof, has been actively carried out.

Being an active energy ray curable resin, urethane acrylate is expected to be used widely for coating on various substrates, a hard coating agent, an adhesive, a cohesive agent, a sealing agent, an ink, or the like. However, a huge problem lies in that structure design of a compound to meet the various needs and adjustment of a composition blend to satisfy the expected properties have not progressed sufficiently. Namely, it is very difficult to maintain balance between the physical properties like toughness, elongation property, high hardness, and high adhesion property of the urethane structure and the physical properties like curing rate according to active energy ray curing, surface dryness and surface hardness after curing, scratch resistance, and curing shrinkage property. As a result, presently there is no resin that can satisfy the required high performances when the target is to achieve both the thin film and high function in a rapidly growing field, for example, adhesion of an optical film in display and touch panel field, hard coating for film including decoration field to optical field, hard coating field, and optical cohesive layer field.

For example, in Patent Literature 1, a photocurable resin composition containing, as an essential component, urethane acrylate with functionality of 6 or higher is disclosed. A cured coating film with tack-free surface, excellent hardness, scratch resistance, and chemical resistance by using this composition is disclosed. Furthermore, suggested in Patent Literature 2 is adduct type urethane acrylamide which is obtained by reacting acrylamide containing a hydroxyl group with polyisocyanate. Also suggested in Patent Literature 2 is oligomer type urethane acrylamide having polyol skeleton which is obtained by a reaction additionally including polyol. As disclosed in Patent Literature 2, by modifying the polymerizable group from an acrylate group to an acrylamide group, the curing rate of the adduct type is enhanced by two times or more. Furthermore, the curing property and stickiness on cured film surface of an oligomer type are improved. Furthermore, in Patent Literature 3, a windable hard coating film for molding that can have suppressed tack and blocking in non-cured state by using an active energy ray curable resin obtained by a reaction between acrylamide containing a hydroxyl group and an isocyanate compound is disclosed. Furthermore, in Patent Literature 4, a hard coating layer of an in-mold molded film having excellent surface hardness and bending property by using a curable resin composition containing acrylamide containing a hydroxyl group, trimethylol propane, a polyvalent isocyanate compound, and a reaction catalyst is disclosed.

However, in none of those Patent Literatures 1 to 4, mention is made regarding the curing resistant shrinkage property and bending resistance. Furthermore, nothing is described regarding the solubility at the time of use in combination with general purpose monomers and oligomers, or resins, and also regarding the transparency of a cured layer obtained therefrom. As such, the aforementioned problems are not solved in the present state.

In Patent Literatures 5 and 6, an oligomer or a polymer of urethaneacrylamide, which is obtained by reacting acrylamide containing a hydroxyl group, polyol, and isocyanate, is used. In Patent Literature 5, an optical film having excellent heat resistant stability is disclosed. In Patent Literature 6, a material for electrophotographic device by which crack prevention can be achieved due to increased strength is disclosed. In Patent Literature 5, an optical film having specific structural unit as being a urethane acrylamide polymer obtained by using specific polyol and specific isocyanate, and achieving the high heat resistance of the film are disclosed. In Patent Literature 6, by containing an acrylamide group, enhancement of fracture strength, improvement of a curing property, and a property of preventing cracks as a result of them are provided. However, in those Patent Literatures, the curing resistant shrinkage property, bending resistance, solubility, and transparency are not described. The aforementioned problem of not having the balance of the urethane acrylamide compound and the problem of not being able to respond to the high performances that are required in rapidly growing fields still remain unsolved.

CITATION LIST

Patent Literature

PATENT LITERATURE 1: JP 2005-281412 A
PATENT LITERATURE 2: JP 2002-37849 A
PATENT LITERATURE 3: JP 2009-244460 A
PATENT LITERATURE 4: JP 2010-128417 A
PATENT LITERATURE 5: JP 2011-218616 A
PATENT LITERATURE 6: JP 2012-82288 A

SUMMARY OF THE INVENTION

Problems to be Solved by the Invention

The first subject is to provide a urethane modified (meth) acrylamide compound which has excellent compatibility with organic solvents and general purpose acrylic monomers and oligomers, and also has a high curing property with an active energy ray and low curing shrinkage rate. The second subject is to provide an active energy ray curable resin containing the urethane modified (meth)acrylamide compound which has an excellent surface dryness (tack resistance), scratch resistance, bending resistance, and curing resistant shrinkage property (curl resistance), as well as high transparency and a high adhesion property.

Solution to the Problems

The inventors of the present invention repeated intensive studies to solve the problems described above. As a result, it was found that the object can be achieved by using a urethane modified (meth)acrylamide compound which has one or more urethane bonds and one or more (meth)acrylamide groups in the molecule, number average molecular weight of 250 to 4,500, and (meth)acryl equivalents within the range of from 250 to 3,000. The present invention is completed accordingly.

Namely, the present invention provides the followings.

General formula [1]

Effects of the Invention

According to the present invention, the urethane modified (meth)acrylamide compound having one or more urethane bonds and one or more (meth)acrylamide groups in the molecule has excellent compatibility with organic solvents and general purpose acrylic monomers and oligomers, and it has a high curing property with an active energy ray and a low curing shrinkage property. Furthermore, according to the present invention, an active energy ray curable resin composition having an excellent surface curing property, bending resistance, scratch resistance, and curing resistant shrinkage property, as well as high transparency and a high adhesion property by containing the urethane modified (meth)acrylamide compound, and a molded article thereof can be provided.

DETAIL DESCRIPTION OF THE EMBODIMENT

Hereinbelow, the present invention is explained in detail.

The urethane modified (meth)acrylamide compound of the present invention has one or more urethane bonds and one or more (meth)acrylamide groups in the molecule. This compound is obtained according to an addition reaction of an alcohol compound having one or more hydroxyl groups per molecule, an isocyanate compound having two or more isocyanate groups per molecule, and N-substituted (meth)acrylamide containing a hydroxyl group. The urethane modified (meth)acrylamide compound preferably has a number average molecular weight of 250 or more but less than 4,500, and (meth)acryl equivalents within the range of from 250 or more to less than 3,000.

The alcohol compound used for synthesis of the urethane modified (meth)acrylamide compound of the present invention is an alcohol compound which has at least one skeleton selected from an ether skeleton, an ester skeleton, a carbonate skeleton, a silicone skeleton, an olefin skeleton, and an acryl skeleton.

The alcohol compound having an ether skeleton includes an ether skeleton in the molecule and also has one or more hydroxyl groups in the end or side chain. Examples of a commercially available product include diethylene glycol, dipropylene glycol, dibutylene glycol, PTMG series, for example, PTMG650 (manufactured by Mitsubishi Chemical Corporation), SANNIX PP, and GP, GOP series, for example, SANNIX PP-1000, GP-250, and GOP-600 (manufactured by Sanyo Kasei Kogyo K.K.), PEG series, for example, PEG300, UNIOX series, UNIOL D, TG, HS, and PB series, for example, UNIOL D-700, TG-1000, HS-1600D, and PB-700, UNILUBE DGP series, POLYCERIN DC, and DCB series (manufactured by NOF Corporation).

The alcohol compound having an ester skeleton includes an ester skeleton in the molecule and also has one or more hydroxyl groups in the end or side chain. Examples of a commercially available product include Kuraray Polyol P, F, N, PMNA series, for example, Kuraray Polyol P-1010, N-2010, and PMNA-2016 (manufactured by Kuraray Co., Ltd.), PRAXEL series, for example, PRAXEL 205 (manufactured by Daicel Corporation), PRIPLAST series, for example, PRIPLAST 1900 (manufactured by Croda Japan), and TESLAC series, for example, TESLAC 2456 (manufactured by Hitachi Chemical Co., Ltd.).

The alcohol compound having a carbonate skeleton includes a carbonate skeleton in the molecule and also has one or more hydroxyl groups in the end or side chain. Examples of a commercially available product include PRAXEL CD series, for example, PRAXEL CD210 (manufactured by Daicel Corporation), ETERNACOLL UH, UHC, UC and UM series, for example, ETERNACOLL UH-100, UHC 50-100, UC-100, and UM-90(3/1) (manufactured by Ube Industries), DURANOL T and G series, for example, DURANOL T6001 (manufactured by Asahi Kasei Chemicals Corporation), NIPPOLLAN series, for example, NIPPOLLAN981 (manufactured by Tosoh Corporation), and Kuraray Polyol C series, for example, Kuraray Polyol C-590 (manufactured by Kuraray Co., Ltd.).

The alcohol compound having a silicone skeleton includes a siloxane bond in the main chain skeleton of a molecule and also has one or more hydroxyl groups in both ends or side chain. Examples of a commercially available product include KF-6000, X-21-5841 (manufactured by Shin Etsu Chemical Co., Ltd.), BY 16-201 manufactured by Toray Dow Corning), XF42-B0970 (manufactured by Momentive Performance Materials), and SILAPLANE series, for example, SILAPLANE FM-0411 (manufactured by JNC Corporation).

The alcohol compound having an olefin skeleton is a compound which includes, in the molecule, a conjugated or non-conjugated olefin skeleton, or a hydrogenated skeleton thereof, and also has one or more hydroxyl groups in the end or side chain. Examples of a commercially available product include NISSO-PB series such as NISSO-PB G-1000 or GI-1000 (manufactured by Nippon Soda Co., Ltd.), Poly bd series (manufactured by Idemitsu Kosan Co., Ltd.), KRASOL series such as KrasolLBH2000 or HLBH-P2000 (manufactured by Cray Valley), and PRIPOL series (manufactured by Croda Japan).

The alcohol compound having an acryl skeleton is a polymer which is obtained by polymerizing one or more kinds of an acrylic monomer, and it is a compound which has one or more hydroxyl groups in the end or side chain of the molecule. Examples thereof include a homopolymer obtained by using an acrylic monomer having a hydroxyl group such as hydroxyacryl (meth)acrylate or hydroxyacryl (meth)acrylamide and a copolymer with a monomer having other unsaturated group. Examples of a commercially available product include UMM-1001 and UT-1001 (manufactured by Soken Chemical & Engineering Co., Ltd.).

One kind among the alcohol compounds having various skeletons as described above may be used singly. Alternatively, it is also possible that an alcohol compound with the same skeleton or two or more kinds of an alcohol compound with different skeleton are used in combination.

The isocyanate compound used for synthesis of the urethane modified (meth)acrylamide compound of the present invention has two or more isocyanate groups in one molecule. Examples thereof include aliphatic isocyanates such as trimethylene diisocyanate, hexamethylene diisocyanate, 1,2-butylene diisocyanate, or 2,4,4-trimethylhexamethylene diisocyanate, aromatic isocyanates such as 1,4-phenylene diisocyanate, 2,4-tolylene diisocyanate, 4,4'-diphenylmethanediisocyanate, and xylylene diisocyanate, alicyclic isocyanates such as cyclohexylene diisocyanate, isophorone diisocyanate, 4,4'-dicyclohexylmethanediisocyanate, 2,5-norbornane diisocyanate, or 2,6-norbornane diisocyanate, and allophanate group-containing isocyanates such as "DESMODUL XP2565" (manufactured by Sumika Bayer Urethane Co., Ltd.) or a multimer such as an adduct type, an isocyanurate type, or a biuret type thereof, for example, Coronate L, HL, HX (manufactured by Nippon Polyurethane Industry Co., Ltd.), and DURANATE 24A-100 (manufactured by Asahi Kasei Corporation).

One kind of those isocyanate compounds may be used either singly or in combination of two or more kinds thereof.

The N-substituted (meth)acrylamide containing a hydroxyl group, which is used for synthesis of the urethane modified (meth)acrylamide compound of the present invention, is a compound represented by the general formula [1]. In the formula, $R_1$ represents a hydrogen atom or a methyl group. $R_2$ and $R_3$ may be the same or different from each other. $R_2$ and $R_3$ may be substituted with a hydrogen atom or a hydroxyl group. $R_2$ and $R_3$ represent a linear or branched alkyl group having 1 to 6 carbon atoms or an aliphatic ring or an aromatic ring having 3 to 6 carbon atoms. Furthermore, $R_2$ and $R_3$ may form, together with the nitrogen atom to which they are attached, a saturated or unsaturated 5- to 7-membered ring. In this 5- to 7-membered ring, an oxygen atom or a nitrogen atom other than the aforementioned nitrogen atom may be additionally contained. However, a case where both $R_2$ and $R_3$ are a hydrogen atom is excluded. Furthermore, a case where both $R_2$ and $R_3$ are an alkyl group is also excluded. Furthermore, $R_2$ and $R_3$ have one or more hydroxyl groups in total.

General formula [1]

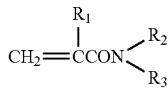

Specific examples of the N-substituted (meth)acrylamide containing a hydroxyl group include N-hydroxymethyl (meth)acrylamide, N-hydroxyethyl (meth)acrylamide, N-hydroxypropyl (meth)acrylamide, N-hydroxyisopropyl (meth)acrylamide, N-methylhydroxymethyl (meth)acrylamide, N-methylhydroxyethyl (meth)acrylamide, N-ethylhydroxymethyl (meth)acrylamide, N-ethylhydroxyethyl (meth)acrylamide, N-ethylhydroxyisopropyl (meth)acrylamide, N-propylhydroxymethyl (meth)acrylamide, N-propylhydroxyisopropyl (meth)acrylamide, N-isopropylhydroxyethyl (meth)acrylamide, N,N-dihydroxymethyl (meth) acrylamide, N,N-dihydroxyethyl (meth)acrylamide, N,N-dihydroxypropyl (meth)acrylamide, N,N-dihydroxyisopropyl (meth)acrylamide, N-[2-(3,4-dihydroxyphenyl)ethyl]acrylamide, 4-(hydroxy) methacrylanilide, N-[1,1-bis(hydroxymethyl)ethyl] acrylamide, N-[1-(hydroxymethyl)propyl]methacrylamide, N-(2-hydroxyphenyl)methacrylamide, N-(2-hydroxy-5-methylphenyl)acrylamide, 1-[4-(2-hydroxyethyl)-1-piperazinyl]-2-propen-1-one, and 1-acryloyl-4-hydroxypiperidine. Furthermore, by using the acrylamide containing a hydroxyl group, the curing property of the urethane modified acrylamide compound to be obtained can be enhanced, and the effect of improving stickiness on a surface of coating film formed therefrom can be suitably increased, in particular. One of those N-substituted (meth)acrylamides containing a hydroxyl group may be used either singly or in combination of two or more kinds thereof.

The method for synthesizing the urethane modified acrylamide compound of the present invention is not particularly limited, and the compound can be synthesized by a known technique for urethanization. With regard to the blending ratio of raw materials, total of the hydroxyl groups is preferably more than the equivalents relative to the total of the isocyanate groups. In particular, a reaction at a ratio so as to have hydroxyl groups in alcohol compound/isocyanate groups/hydroxyl groups in (meth)acrylamide=1/1/1.5 to 1/3/2.5 is particularly preferable. If the blending ratio of the isocyanate groups is above the range, there is a possibility that thickening or coloration over time of the urethane modified acrylamide compound is caused. Meanwhile, if the hydroxyl groups in (meth)acrylamide is above the range, there is a possibility the water resistance and moisture resistance of the urethane modified acrylamide compound to be obtained are deteriorated.

The urethanization reaction of the present invention can be carried out by a known method. Namely, the alcohol compound as a raw material, an isocyanate compound and N-substituted (meth)acrylamide containing a hydroxyl group are admixed with each other, and, subsequently, the temperature of the reaction solution is increased to perform the reaction. It is desirable that this reaction is performed at a temperature of 10 to 160° C., and preferably at a temperature of 20 to 140° C. The mixing of the raw materials can be performed either in one step or in several divided steps. In addition, the reaction can be performed in the absence of a solvent. However, as necessary, the reaction can be performed in an organic solvent or in a reactive diluent. Examples of the solvent which can be used include acetone, methyl ethyl ketone, methyl isobutyl ketone, cyclohexanone, dimethyl formamide, dimethyl acetamide, dimethyl sulfoxide, ethyl acetate, butyl acetate, tetrahydrofuran, hexane, cyclohexane, benzene, toluene, xylene and aliphatic hydrocarbon-based solvents (petroleum ether), and the reaction can be performed in the presence of the above solvent. The reactive diluent which can be used is not particularly limited as long as it does not react with isocyanate or a hydroxyl group, and examples thereof include methyl acrylate, ethyl acrylate, butyl acrylate, 2-ethylhexyl acrylate, long chain aliphatic acrylate, allyl acrylate, cyclohexyl acrylate, 1,6-hexane diacrylate, tetraethylene glycol diacrylate, dipentaerythritol hexaacrylate, trimethylol propane triacrylate, isobornyl acrylate, dimethyl aminoethyl acrylate, diethyl aminoethyl acrylate, dimethyl acrylamide, diethyl acrylamide, and N-acryloylmorpholine. The use amount of an organic solvent or a reactive diluent is 0 to 400% by weight, and suitably 0 to 200% by weight relative to the isocyanate compound.

In the urethanization reaction, a catalyst can be added for the purpose of accelerating the reaction. Examples of the catalyst include a potassium or sodium salt of alkylphosphonic acid, metal salts such as a sodium salt, a potassium salt, a nickel salt, a cobalt salt, a cadmium salt, a barium salt, a calcium salt, and a zinc salt of fatty acids having 8 to 20 carbon atoms, and organic tin compounds such as dibutyl tin dilaurate, dioctyl tin maleate, dibutyl dibutoxy tin, bis(2-ethylhexyl) tin oxide, and 1,1,3,3-tetrabutyl-1,3-diacetoxy-distannoxane, and tertiary amine compounds such as N,N,N',N'-tetramethylguanidine, 1,3,5-tris(N,N-dimethylaminopropyl)hexahydro-S-triazine, 1,8-diazabicyclo[5.4.0]undecene-7, N,N'-dimethylpiperazine, N-ethylmorpholine, N,N-dimethylethanolamine, 1-methyl imidazole, and triethylene diamine. They may be used either singly or in combination of two or more types thereof. The use amount of the catalyst is preferably usually 1% by weight or less, and more preferably 0.1% by weight or less, relative to the total weight of the raw material components.

In order to suppress radical polymerization caused by the double bond of the N-substituted (meth)acrylamide containing a hydroxyl group and the double bond of the urethane modified (meth)acrylamide to be obtained, a radical polymerization inhibitor can be used as necessary. Examples of the radical polymerization inhibitor include quinone-based polymerization inhibitors such as hydroquinone, methoxy-hydroquinone, benzoquinone and p-tert-butylcatechol; alkyl phenol-based polymerization inhibitors such as 2,6-di-tert-butylphenol, 2,4-di-tert-butylphenol, 2-tert-butyl 4,6-dimethylphenol, 2,6-di-tert-butyl-4-methylphenol and 2,4,6-tri-tert-butylphenol; amine-based polymerization inhibitors such as alkylated diphenylamine, N,N'-diphenyl-p-phenylenediamine, and phenothiazine, and N-oxyls such as 4-hydroxy-2,2,6,6-tetramethylpiperidine-N-oxyl; and copper dithiocarbamate-based polymerization inhibitors such as copper dimethyl dithiocarbamate, copper diethyl dithiocarbamate and copper dibutyl dithiocarbamate. Among them, the salt may be used either singly, or two or more kinds thereof may be used in combination.

The addition amount of these polymerization inhibitors may be suitably set depending on the kind, the blending amount or the like of the N-substituted (meth)acrylamide containing a hydroxy group. From the viewpoint of polymerization preventing effects, convenience in production, and economic efficiency, the addition amount is preferably usually 0.001 to 5% by weight, and more preferably 0.01 to 1% by weight, relative to urethane modified (meth)acrylamide to be obtained.

The number average molecular weight of the urethane modified (meth)acrylamide of the present invention is preferably 250 or more but less than 4,500, and more preferably 250 or more but less than 3,000. When the number average molecular weight is less than 250, ratio of the components for monofunctional small molecule is high. As such, there is a possibility that the urethane modified (meth)acrylamide to be obtained has lower curing property, or lower solubility in organic solvents and general purpose acrylic monomers. On the other hand, the number average molecular weight of more than 4,500 is not desirable in that, due to a decreased crosslinking density, the curing property and tack resistance are not satisfied at sufficient level.

The acryl equivalents of the urethane modified (meth) acrylamide of the present invention is preferably from 250 or more to less than 3,000, and more preferably from 250 to 2,500. When the acryl equivalents is less than 250, the density of (meth)acrylamide group as a polymerizable group is high. Due to such reasons, it becomes easier to have an occurrence of troubles like polymerization during the process for producing the urethane modified (meth)acrylamide and storage after the production. On the other hand, the acryl equivalents of more than 3,000 is not desirable in that, due to a decreased crosslinking density, the curing property and tack resistance are not satisfied at sufficient level.

The acryl equivalents of the urethane modified (meth) acrylamide having an ether skeleton of the present invention is preferably within the range of from 250 to 750. When the acryl equivalents of the urethane modified (meth)acrylamide having an ether skeleton is less than 250, it is undesirable as described in the above. On the other hand, when the acryl equivalents is more than 750, it becomes difficult to form an intermolecular or intramolecular hydrogen bond in the urethane modified (meth)acrylamide. As a result, there is a possibility that a decrease in curing rate is caused.

In a case where the urethane modified (meth)acrylamide system of the present invention is used alone, depending on the alcohol-derived skeleton, the type of (meth)acrylamide groups, the acryl equivalents, and the molecular weight, physical properties and performances such as the active energy ray curing property, surface dryness (tack resistance) of a cured film to be obtained, and adhesion property to various substrates are different.

The urethane modified (meth)acrylamide of the present invention can be completely cured by irradiation with active energy rays. The active energy ray irradiation amount required (cumulative amount of light) varies depending on the type of (meth)acrylamide group and acryl equivalents. The active energy ray irradiation amount (cumulative amount of light) is preferably 0.1 to 2,000 mJ/cm$^2$, and particularly preferably about 1 to 1,000 mJ/cm$^2$. If the cumulative amount of light is less than 0.1 mJ/cm$^2$, insufficiently cured portions remain, and, as a result, there is a possibility that the overall hardness, water resistance, or durability of a cured product deteriorate. In addition, if the cumulative amount of light is greater than 2,000 mJ/cm$^2$, side reactions such as decomposition occur due to excess energy, and there is a tendency that the cured film is easily colored.

The water absorption rate of a cured film formed of the urethane modified (meth)acrylamide of the present invention is preferably 2% or less, and particularly preferably 1% or less. If the water absorption rate is greater than 2%, in the case of using for a long period of time under a high humidity environment, water absorption by the cured film occurs over time. Therefore, there is a possibility that distortion of the shape of the cured film caused by swelling of the water-absorbing cured film, resulting in deterioration of the adhesion property and transparency.

The curing shrinkage rate of the urethane modified (meth) acrylamide of the present invention can be evaluated by using the floating height of a cured film caused by ultraviolet ray irradiation (evaluation of curl resistance). According to the evaluation, the floating height is preferably 1 cm or less, and particularly preferably 0.5 cm or less. When the floating of a cured film is more than 1 cm, the adhesion property to a substrate is impaired as caused by film distortion. As a result, the water resistance, durability, and bending resistance of a curable resin composition containing the urethane modified (meth)acrylamide, and those of a molded article using the composition may easily get deteriorated. Furthermore, there is a possibility that the shape is not stably maintained.

Examples of the polyfunctional (meth)acrylate compound (B) used in the present invention is either polyfunctional (meth)acrylate or polyfunctional (meth)acrylamide. Examples thereof include monomers and oligomers of alkylene glycol di(meth)acrylate such as ethylene glycol di(meth)acrylate, dicyclopentanyl di(meth)acrylate, caprolactone modified dicyclopentenyl di(meth)acrylate, pentaerythritol tetra(or tri)(meth)acrylate, pentaerythritol tri(meth)acrylate, dipentaerythritol hexa(meth)acrylate, dipentaerythritol penta(meth)acrylate, trimethylol propane tri(meth)acrylate, ethylene oxide modified bisphenol A di(meth)acrylate, cyclohexanedimethanol di(meth)acrylate, acrylate ester (dioxane glycol diacrylate), alkoxylated hexane diol di(meth)acrylate, alkoxylated (cyclo)hexane dimethanol di(meth)acrylate, epoxy (meth)acrylate, urethane (meth)acrylate, and urethane (meth)acrylamide. Furthermore, the polyfunctional (meth) acrylate may be used either singly, or two or more kinds thereof may be used in combination.

The monofunctional (meth)acryl compound (C) to be used in the present invention is either monofunctional (meth)acrylate or monofunctional (meth)acrylamide. Furthermore, if necessary, a polymerizable quaternary salt ionic compound may be contained therein. Furthermore, the monofunctional (meth)acryl compound may be used either singly, or two or more kinds thereof may be used in combination.

Examples of the monofunctional (meth)acrylate include alkyl (meth)acrylate such as methyl (meth)acrylate, hydroxyethyl acrylate, alkoxyethyl (meth)acrylate, methoxy diethylene glycol (meth)acrylate, 2-(2-ethoxyethoxy)ethyl acrylate, phenoxyethyl (meth)acrylate, cyclohexyl (meth)acrylate, benzyl (meth)acrylate, phenoxyethyl (meth)acrylate, dicyclopentanyl (meth)acrylate, isobornyl (meth)acrylate, tetrahydrofurfuryl acrylate, 2-methyl-2-adamantyl (meth)acrylate, allyl (meth)acrylate, and hydroxyalkyl (meth)acrylate such as hydroxyethyl (meth)acrylate.

Examples of the monofunctional (meth)acrylamide used in the present invention include N-alkyl (meth)acrylamide, N-alkoxyacryl (meth)acrylamide, N-vinylpyrrolidone, N-vinylcaprolactam, N-[3-(dimethylamino)]propylacrylamide, N,N-dimethyl (meth)acrylamide, N,N-diethyl (meth)acrylamide, N-acryloylmorpholine, and hydroxyalkyl (meth) acrylamide such as hydroxyethylacrylamide.

Preferably, the urethane modified (meth)acrylamide compound (A) of the present invention is contained at 1% by weight or more in the active energy ray curable resin composition. When the content is less than 1% by weight, there is a possibility that favorable surface curing property, bending resistance, scratch resistance, or the like are not obtained. Furthermore, the content of the polyfunctional (meth)acryl compound (B) in the curable resin composition is preferably 90% by weight or less. When the content of (B) is more than 90% by weight, liquid viscosity of the curable resin composition increases, and it becomes difficult to achieve the mixing and coating. Namely, a problem occurs in terms of the handling. For such reasons, the content of (B) that is higher than 90% by weight is not desirable. Furthermore, when the monofunctional (meth)acryl compound (C) is blended in the curable resin composition, content of 90% by weight or less is desirable to maintain sufficient scratch resistance and curing property.

In the active energy ray curable resin composition of the present invention, a polymerizable quaternary salt ionic compound may be added. Examples thereof include ionic vinyl monomers, oligomers and polymers having them as constitutional components. The ionic vinyl monomer is an onium salt obtained by combining a cation and an anion. Specific examples of the cation include (meth)acrylate-based or (meth)acrylamide-based ammonium ions and imidazolium ions. Examples of the anions include halogen ions such as $Cl^-$, $Br^-$ and $I^-$, inorganic acid anions or organic acid anions such as $OH^-$, $CH_3COO^-$, $NO_3^-$, $ClO_4^-$, $PF_6^-$, $BF_4^-$, $HSO_4^-$, $CH_3SO_3^-$, $CF_3SO_3^-$, $CH_3C_6H_6SO_3^-$, $C_4F_9SO_3^-$, $(CF_3SO_2)_2N^-$, and $SCN^-$.

The ion of the polymerizable quaternary salt ionic compound can easily form a hydrogen bond and an ionic bond with a substrate for coating, and it can provide conductivity or anti-static property. As a result, the wettability is enhanced. Accordingly, more homogeneous coating can be achieved. As a result, the film can be formed more stably. Furthermore, the polymerizable quaternary salt ionic compound itself is an active energy ray curable compound. For such reasons, according to copolymerization with an active energy ray curable resin composition, a secondary effect like providing permanent conductivity or anti-static property is obtained without having a bleed-out. Furthermore, the effect of enhancing the adhesion property is provided. The blending amount of those ionic compounds can be adjusted depending on the number of the functional groups and molecular weight of an ion pair. For such reasons, the blending amount is not particularly limited. In general, the ionic compound is added preferably at 0 to 50% by weight, and particularly preferably at 0 to 10% by weight relative to the active energy ray curable resin composition. If the blending amount of the ionic compound is greater than 50% by weight, there is a possibility that the deterioration of transparency of a cured film is caused although it depends also on the type of the ionic compound.

The active energy ray of the present invention is defined as energy ray which can generate an active species by decomposing a compound (photopolymerization initiator) which generates an active species. Examples of such an active energy rays include light energy rays such as visible light, an electron beam, ultraviolet rays, infrared rays, X-rays, α-rays, β-rays, and γ-rays.

When curing the active energy ray curable resin composition of the present invention, a photopolymerization initiator is added. The photopolymerization initiator is not particularly necessary in the case of using an electron beam as active energy ray. However, the photopolymerization initiator is necessary when ultraviolet rays are used. The photopolymerization initiator may be suitably selected from usual photopolymerization initiators such as an acetophenone-based photopolymerization initiator, a benzoin-based photopolymerization initiator, a benzophenone-based photopolymerization initiator and a thioxanthone-based photopolymerization initiator. Among the photopolymerization initiators, examples of commercially available photopolymerization initiators which can be used include product named Irgacure 1173, Irgacure 184, Irgacure 369, Irgacure 500, Irgacure 651, Irgacure 754, Irgacure 819, Irgacure 907, Irgacure 2959, and Irgacure TPO manufactured by BASF JAPAN, and product named Ubecryl P36 manufactured by UCB Chemicals. These photopolymerization initiators can be used either singly or in combination of two or more types thereof.

The use amount of the photopolymerization initiator is not particularly limited. In general, 0 to 10% by weight of the photopolymerization initiator is preferably added, and 1 to 5% by weight of the photopolymerization initiator is more preferably added, relative to the active energy ray curable resin composition. If the addition amount is greater than 10% by weight, there is a possibility that deterioration of the strength or yellowing of the coating film is caused.

In a range in which the characteristics of the active energy ray curable resin composition of the present invention and the molded article produced from the same are not deteriorated, other arbitrary components such as a pigment, a dye, a surfactant, an anti-blocking agent, a leveling agent, a dispersing agent, a defoamer, an antioxidant, an ultraviolet sensitizer or a preservative may be used in combination.

According to irradiation with an active energy ray, the active energy ray curable resin composition of the present invention applied on the surface of a substrate or between substrates, such as paper, fabric, nonwoven fabric, glass, plastics including polyethylene terephthalate, diacetate cellulose, triacetate cellulose, an acrylic polymer, polyvinyl chloride, cellophane, celluloid, polycarbonate and polyimide, and metals, curing of the composition can be achieved. Accordingly, it is possible to obtain a coating layer, an ink layer, a cohesive layer, or an adhesive layer, each having high performance. In particular, the active energy ray curable resin composition of the present invention has a urethane oligomer having high transparency, and thus the resin composition can be officially used as an optical resin composition such as an optical cohesive, an optical adhesive, or a coating material of an optical film. As the method of applying this usable resin composition on a substrate, a normal coating film formation method such as a spin coating method, a spray coating method, a dipping method, a gravure roll method, a knife coating method, a reverse roll method, a screen printing method, or a bar coater method can be mentioned. In addition, as the method of applying between substrates, a lamination method, a roll-to-roll method, and the like can be mentioned.

EXAMPLES

Hereinbelow, the present invention is described in detail and more specifically in with reference to synthesis examples and evaluation examples, but the present invention is not limited to the examples. Furthermore, in the followings, % other than yield indicates % by weight. Physical property analysis of the obtained urethane modified (meth) acrylamide was performed by the following methods.
(1) Measurement of Molecular Weight and Calculation of Acryl Equivalents The number average molecular weight of the obtained urethane modified (meth)acrylamide or the like was measured by high-performance liquid chromatography ("LC-10A" manufactured by Shimadzu Corporation, column: Shodex GPC KF-803L (exclusion limit molecular weight: $7 \times 10^4$, separation range: 100 to $7 \times 10^4$, theoretical plate number: 18,000 plates/piece (set), filler material: styrene-divinylbenzene copolymer, filler particle size: 10 eluent: tetrahydrofuran) and calculated by a standard polystyrene molecular weight conversion method. Furthermore, the acryl equivalents (molecular weight per (meth)acrylamide group) was also calculated.
(2) Measurement of Viscosity 1 part by weight of the obtained urethane modified (meth)acrylamide or the like was homogeneously admixed with 1 part by weight of tetrahydrofuran. By using a cone-plate type viscometer (device name: "RE550 viscometer" manufactured by Toki Sangyo Co., Ltd.), the solution viscosity at 25° C. was measured according to JIS K5600-2-3.

Synthesis examples of the urethane modified (meth)acrylamide compound (A) are described hereinbelow.

Synthesis Example 1. Synthesis of Urethane Modified (meth)acrylamide UY-1

Into a 300 mL four-neck flask provided with a stirrer, a thermometer, a condenser and a dry gas inlet tube, 44.4 g (0.2 mol) of isophorone diisocyanate (IPDI), 90 g (0.09 mol) of ETERNACOLL UC-100 (polycarbonate polyol, manufactured by Ube Industries, number average molecular weight of 1,000), 5.4 g (0.01 mol) of PRIPOL 2033 (dimer diol, manufactured by Croda Japan, number average molecular weight of 540), 48.6 g of methyl ethyl ketone (MEK), and 0.08 g of dibutylhydroxytoluene (BHT) were added. Then, while performing flushing with dry nitrogen, the temperature was raised to 70° C. After that, 16.2 mg of dibutyl tin dilaurate was added dropwise thereto. The reaction was carried out for 4 hours at 70° C. Next, 23.0 g (0.2 mol) of hydroxyethyl acrylamide (manufactured by KJ Chemicals Corporation, registered trademark "HEAA") was added thereto. Under a dry air stream, the resulting product was continuously stirred for 3 hours while maintaining the temperature in the system at 80° C. The solvent was distilled off according to a reduced pressure method. As a liquid with viscosity, 161.9 g of UY-1 was obtained. According to an infrared absorption spectrum (IR) analysis, it was found that the absorption (2260 cm$^{-1}$) specific to the isocyanate group of IPDI as a raw material is completely lost. Furthermore, specific absorption (1,650 cm$^{-1}$) of the amide group derived from "HEAA" and specific absorption (1,740 cm$^{-1}$) of the urethane bond generated were detected. Based on the result, generation of a target urethane modified (meth)acrylamide UY-1 was confirmed. The number average molecular weight of the obtained UY-1 was 1,600. The acryl equivalents of UY-1 was 800. Furthermore, the solution viscosity at 25° C. was found to be 20 mPa·s.

Synthesis Example 2. Synthesis of Urethane Modified (Meth)Acrylamide UY-2

The same apparatus as that of Synthesis Example 1 was used. 17.5 g (0.025 mol) of UNILUBE DGP-700F (polyether polyol, tetrafunctional, manufactured by NOF Corporation, number average molecular weight of 700), 50 g (0.1 mol) of ETERNACOLL UH-50 (polycarbonate polyol, manufactured by Ube Industries, number average molecular weight of 500), 52.4 g (0.2 mol) of hexamethylene diisocyanate (HDI), 39.4 g of MEK, and 0.07 g of BHT were added.

While performing flushing with dry nitrogen, the temperature was raised to 65° C. After that, 0.13 g of triethylene diamine was added dropwise thereto. The reaction was carried out for 5 hours at 65° C. Next, 11.5 g (0.1 mol) of "HEAA" was added thereto. Under a dry air stream, the resulting product was continuously stirred for 3 hours while maintaining the temperature in the system at 65° C. The solvent was distilled off according to a reduced pressure method. As a liquid with viscosity, 131.4 g of UY-2 was obtained. In the same manner as Synthesis Example 1, according to an IR analysis, generation of a target urethane modified (meth)acrylamide UY-2 was confirmed. The number average molecular weight of the obtained UY-2 was 4,480. The acryl equivalents was 1,120. Furthermore, the solution viscosity at 25° C. was found to be 35 mPa·s.

Synthesis Example 3. Synthesis of Urethane Modified (Meth)Acrylamide UY-3

The same apparatus as that of Synthesis Example 1 was used. 16.8 g (0.1 mol) of dicyclohexylmethane-4,4'-diisocyanate (hydrogenated MDI), 50 g (0.05 mol) of UMMA-1001 (acryl polyol(methyl acrylate main skeleton, monofunctional, manufactured by Soken Chemical & Engineering Co., Ltd., number average molecular weight of 1,000), 50 g (0.05 mol) of UH-100 (polycarbonate polyol, manufactured by Ube Industries, number average molecular weight of 1000), and 0.06 g of BHT were added.

While performing flushing with dry nitrogen, the temperature was raised to 65° C. After that, 12.3 mg of dibutyl tin dilaurate was added dropwise thereto. The reaction was carried out for 4 hours at 65° C. Next, 5.8 g (0.05 mol) of "HEAA" was added thereto. Under a dry air stream, the resulting product was continuously stirred for 3 hours while maintaining the temperature in the system at 65° C. As a liquid with viscosity, 122.6 g of UY-3 was obtained. In the same manner as Synthesis Example 1, according to an IR analysis, generation of a target urethane modified (meth)acrylamide UY-3 was confirmed. The number average molecular weight of the obtained UY-3 was 2,700. The acryl equivalents was 2,700. Furthermore, the solution viscosity at 25° C. was found to be 23 mPa·s.

Synthesis Example 4. Synthesis of Urethane Modified (Meth)Acrylamide UY-4

The same apparatus as that of Synthesis Example 1 was used. 16.7 g (0.025 mol) of isocyanurate adduct of IPDI (IPDI nurate), 37.5 g (0.075 mol) of Kuraray Polyol P-530 (polyester polyol, manufactured by Kuraray Co., Ltd., number average molecular weight of 500), 24.2 g of MEK, 0.04 g of BHT, and 8.1 mg of dibutyl tin dilaurate were added. After that, while performing flushing with dry nitrogen, 16.7 g (0.075 mol) of IPDI was added dropwise thereto at addition rate which has been adjusted to have a temperature of 65° C. The reaction was carried out for 2 hours at 65° C. Next, 9.7 g (0.08 mol) of N-methylhydroxyethyl acrylamide (MHEAA) was added thereto. Under a dry air stream, the resulting product was continuously stirred for 5 hours while maintaining the temperature in the system at 65° C. The solvent was distilled off according to a reduced pressure method. As a liquid with viscosity, 80.5 g of UY-4 was obtained. In the same manner as Synthesis Example 1, according to an IR analysis, generation of a target urethane modified (meth)acrylamide UY-4 was confirmed. The number average molecular weight of the obtained UY-4 was 3,200. Furthermore, the acryl equivalents was 1,100. Furthermore, the solution viscosity at 25° C. was found to be 28 mPa·s.

Synthesis Example 5. Synthesis of Urethane Modified (Meth)Acrylamide UY-5

The same apparatus as that of Synthesis Example 1 was used. 75 g (0.05 mol) of GI-1000 (butadiene having hydroxyl group at both ends, manufactured by Nippon Soda Co., Ltd., number average molecular weight of 1,500), 34.2 g of MEK, 0.06 g of BHT, and 0.11 g of pentamethyldiethylene triamine were added. After that, while performing flushing with dry nitrogen, 26.2 (0.1 mol) of hydrogenated MDI was added dropwise thereto at addition rate which has been adjusted to have a temperature of 70° C. The reaction was carried out for 4 hours at 70° C. Next, 12.9 g (0.10 mol) of hydroxyethyl methacrylamide (HEMAA) was added thereto. Under a dry air stream, the resulting product was continuously stirred for 4 hours while maintaining the temperature in the system at 70° C. The solvent was distilled off according to a reduced pressure method. As a liquid with viscosity, 114.1 g of UY-5 was obtained. In the same manner as Synthesis Example 1, according to an IR analysis, generation of a target urethane modified (meth)acrylamide UY-5 was confirmed. The number average molecular weight of the obtained UY-5 was 2,250. Furthermore, the acryl equivalents was 1,130. Furthermore, the solution viscosity at 25° C. was found to be 80 mPa·s.

Synthesis Example 6. Synthesis of Urethane Modified (Meth)Acrylamide UY-6

The same apparatus as that of Synthesis Example 1 was used. 50 g (0.05 mol) of KF-6000 (silicone having both ends modified with carbinol, manufactured by Shin Etsu Chemical Co., Ltd., number average molecular weight of 1,000), 21.0 g (0.1 mol) of trimethylhexamethylene diisocyanate (TMHDI), and 0.04 g of BHT were added. While performing flushing with dry nitrogen, the temperature was raised to 70° C. After that, 8.3 mg of dibutyl tin dilaurate was added dropwise thereto. The reaction was carried out for 5 hours at 70° C. Next, 11.5 g (0.1 mol) of "HEAA" was added thereto. Under a dry air stream, the resulting product was continuously stirred for 3 hours while maintaining the temperature in the system at 80° C. As a liquid with viscosity, 82.5 g of UY-6 was obtained. In the same manner as Synthesis Example 1, according to an IR analysis, generation of a target urethane modified (meth)acrylamide UY-6 was confirmed. The number average molecular weight of the obtained UY-6 was 1,700. Furthermore, the acryl equivalents was 830. Furthermore, the solution viscosity at 25° C. was found to be 12 mPa·s.

Synthesis Example 7. Synthesis of Urethane Modified (Meth)Acrylamide UY-7

The same apparatus as that of Synthesis Example 1 was used. 25 g (0.1 mol) of UNIOL D-250 (polypropylene glycol, manufactured by NOF Corporation, number average molecular weight of 250) and 0.04 g of BHT were added. While performing flushing with dry nitrogen, the temperature was raised to 75° C. After that, 8.2 mg of dibutyl tin dilaurate was added dropwise thereto. Further, the reaction with 33.6 g (0.2 mol) of HDI was added to carry out for 3 hours at 75° C. Next, 23.0 g (0.2 mol) of "HEAA" was added thereto. Under a dry air stream, the resulting product was continuously stirred for 3 hours while maintaining the temperature in the system at 75° C. As a liquid with viscosity, 81.6 g of UY-7 was obtained. In the same manner as Synthesis Example 1, according to an IR analysis, generation of a target urethane modified (meth)acrylamide UY-7 was confirmed. The number average molecular weight of the obtained UY-7 was 820. Furthermore, the acryl equivalents was 400. Furthermore, the solution viscosity at 25° C. was found to be 8 mPa·s.

Comparative Synthesis Example 1. Synthesis of Urethane Acrylic Oligomer (UA-1)

The same apparatus as that of synthesis example 1 was used. 100 g (0.05 mol) of DURANOL T4672 (polycarbonate polyol, manufactured by Asahi Kasei Chemicals Corporation, number average molecular weight of 2,000), 11.1 g (0.02 mol) of IPDI nurate, 38.4 g of MEK, and 0.06 g of BHT were added. After raising the temperature to 80° C., 12.8 mg of dibutyl tin dilaurate was added dropwise thereto. While performing, flushing with dry nitrogen, 14.7 g (0.07 mol) of IPDI was added dropwise thereto at addition rate which has been adjusted to have a temperature of 80° C. The reaction was carried out for 4 hours at 80° C. Next, 9.4 g (0.08 mol) of "HEAA" was added thereto. Under a dry air stream, the resulting product was continuously stirred for 3 hours while maintaining the temperature in the system at 80° C. The solvent was distilled off according to a reduced pressure method. As a liquid with viscosity, 135.2 g of UA-1 was obtained. In the same manner as Synthesis Example 1, according to an IR analysis, generation of a urethane acrylic oligomer UA-1 was confirmed. The number average molecular weight of the obtained UA-1 was 7,700. Furthermore, the acryl equivalents was 2,600. Furthermore, the solution viscosity at 25° C. was found to be 250 mPa·s.

Comparative Synthesis Example 2. Synthesis of Urethane Acrylic Oligomer (UA-2)

The same apparatus as that of Synthesis Example 1 was used. 53.3 g (0.13 mol) of UNIOL D-400 (polypropylene glycol, manufactured by NOF Corporation, number average molecular weight of 400), 0.06 g of BHT, and 12.1 mg of dibutyl tin dilaurate were added. After that, while performing flushing with dry nitrogen, 52.4 g (0.2 mol) of hydrogenated MDI was added dropwise thereto at addition rate which has been adjusted to have a temperature of 80° C. The reaction was carried out for 5 hours at 80° C. Next, 15.3 g (0.13 mol) of "HEAA" was added thereto. Under a dry air stream, the resulting product was continuously stirred for 3 hours while maintaining the temperature in the system at 80° C. As a liquid with viscosity, 121.0 g of UA-2 was obtained. In the same manner as Synthesis Example 1, according to an IR analysis, generation of a urethane acrylic oligomer UA-2 was confirmed. The number average molecular weight of the obtained UA-2 was 1,900. Furthermore, the acryl equivalents was 950. Furthermore, the solution viscosity at 25° C. was found to be 24 mPa·s.

Comparative Synthesis Example 3. Synthesis of Urethane Acrylic Oligomer UA-3

The same apparatus as that of Synthesis Example 1 was used. 60 g (0.06 mol) of KF-6000, 26.6 g (0.12 mol) of IPDI, and 0.05 g of BHT were added. After that, while performing flushing with dry nitrogen, the temperature was raised to 80° C. After that, the reaction with 10.1 mg of dibutyl tin laurate was carried out for 4 hours at 80° C. Next, 13.9 g (0.12 mol) of hydroxyethyl acrylate (HEA) was added thereto. Under a dry air stream, the resulting product was continuously stirred for 3 hours while maintaining the temperature in the system at 70° C. As a liquid with viscosity, 100.6 g was obtained. In the same manner as Synthesis Example 1, according to an IR analysis, generation of a urethane acrylic oligomer UA-3 was confirmed. The number average molecular weight of the obtained UA-3 was 1,500. Furthermore, the acryl equivalents was 850. Furthermore, the solution viscosity at 25° C. was found to be 10 mPa·s.

Comparative Synthesis Example 4. Synthesis of Urethane Acrylic Oligomer UA-4

The same apparatus as that of Synthesis Example 1 was used. 13.2 g (0.04 mol) of UNIOL TG-330 (polyoxypropylene glycerin ether, trifunctional, manufactured by NOF Corporation, number average molecular weight of 330), 79.9 g (0.12 mol) of IPDI nurate, 36.3 g of MEK, and 0.06 g of BHT were added. After that, while performing flushing with dry nitrogen, the temperature was raised to 65° C. After that, the reaction with 12.1 mg of dibutyl tin laurate was carried out for 4 hours at 65° C. Next, 27.8 g (0.24 mol) of HEA was added thereto. Under a dry air stream, the resulting product was continuously stirred for 4 hours while maintaining the temperature in the system at 65° C. The solvent was distilled off according to a reduced pressure method. As a solid, 121.0 g of urethane acrylic oligomer UA-4 was obtained. In the same manner as Synthesis Example 1, according to an IR analysis, generation of a urethane acrylic oligomer UA-4 was confirmed. The number average molecular weight of the obtained UA-4 was 3,000. Furthermore, the acryl equivalents was 500. Furthermore, the solution viscosity at 25° C. was found to be 23 mPa·s.

Comparative Synthesis Example 5. Synthesis of Adduct Type Urethane Acrylamide UA-5

With reference to Example 2 of patent Literature 2 (JP 2002-37849 A), synthesis was carried out by reacting 74.8 g (0.43 mol) of tolylene diisocyanate (TDI) and 100 g (0.87 mol) of "HEAA" in 180 g of N,N-dimethyl formamide (DMF) for 4 hours at 40° C. The solvent was distilled off according to a reduced pressure method. As a solid, adduct type urethane acrylamide UA-5 was obtained. The number average molecular weight of the obtained UA-5 was 400, and the solution viscosity at 25° C. was found to be 8 mPa·s.

Synthesis examples of polyfunctional (meth)acryl compound (B) are described hereinbelow.

Synthesis Example 8. Synthesis of Reactive Urethane Polymer UP-1

The same apparatus as that of Synthesis Example 1 was used. 75 g (0.075 mol) of ETERNACOLL UC-100, 51.5 g of MEK, 0.06 g of BHT, and 11.1 mg of dibutyl tin dilaurate were added. After that, while performing flushing with dry nitrogen, the temperature was raised to 65° C. After that, 26.2 g (0.12 mol) of IPDI was added dropwise thereto. The reaction was carried out for 4 hours at 65° C. Next, 10.0 g (0.09 mol) of "HEAA" was added thereto. Under a dry air stream, the resulting product was continuously stirred for 4 hours while maintaining the temperature in the system at 65° C. The solvent was distilled off according to a reduced pressure method. As a viscous liquid, 111.1 g of UP-1 was obtained. In the same manner as Synthesis Example 1, according to an IR analysis, generation of a target reactive urethane polymer UP-1 was confirmed. The number average molecular weight of the obtained UP-1 was 4,700. Furthermore, the acryl equivalents was 1,560. Furthermore, the solution viscosity at 25° C. was found to be 55 mPa·s.

Synthesis Example 9. Synthesis of Reactive Urethane Polymer UP-2

The same apparatus as that of Synthesis Example 1 was used. 8.7 g (0.05 mol) of TDI, 90 g (0.045 mol) of PTMG2000 (polytetramethylene ether glycol, manufactured by Mitsubishi Chemical Corporation, number average molecular weight of 2,000), 50.0 g of MEK, and 0.05 g of BHT were added thereto. While performing flushing with dry nitrogen, the temperature was raised to 75° C. After that, 10.0 mg of dibutyl tin dilaurate was added dropwise thereto.

The reaction was carried out for 3 hours at 75° C. Next, 1.3 g (0.01 mol) of hydroxyethyl methacrylate (HEMA) was added thereto. Under a dry air stream, the resulting product was continuously stirred for 3 hours while maintaining the temperature in the system at 75° C. The solvent was distilled off according to a reduced pressure method. As a viscous liquid, 100.0 g of UP-2 was obtained. In the same manner as Synthesis Example 1, according to an IR analysis, generation of a target reactive urethane polymer UP-2 was confirmed. The number average molecular weight of the obtained UP-2 was 20,000. Furthermore, the acryl equivalents was 10,000. Furthermore, the solution viscosity at 25° C. was found to be 180 mPa·s.

Synthesis Example 10. Synthesis of Reactive Urethane Polymer UP-3

The same apparatus as that of Synthesis Example 1 was used. 11.1 g (0.05 mol) of IPDI, 80 g (0.04 mol) of ETERNACOLL UHC-50-200 (polycarbonate polyol, manufactured by Ube Industries, number average molecular weight of 2,000), 46.7 g of MEK, and 0.05 g of BHT were added thereto. While performing flushing with dry nitrogen, the temperature was raised to 70° C. After that, 9.3 mg of dibutyl tin dilaurate was added dropwise thereto. The reaction was carried out for 4 hours at 70° C. Next, 2.3 g (0.02 mol) of HEA was added thereto. Under a dry air stream, the resulting product was continuously stirred for 4 hours while maintaining the temperature in the system at 70° C. The solvent was distilled off according to a reduced pressure method. As a viscous liquid, 93.4 g of UP-3 was obtained. In the same manner as Synthesis Example 1, according to an IR analysis, generation of a target reactive urethane polymer UP-3 was confirmed. The number average molecular weight of the obtained UP-3 was 9,000. Furthermore, the acryl equivalents was 4,600. Furthermore, the solution viscosity at 25° C. was found to be 80 mPa·s.

Synthesis Example 11. Synthesis of Reactive Urethane Polymer UP-4

The same apparatus as that of Synthesis Example 1 was used. 1.11 g (2 mmol) of IPDI nurate, 11.1 g (50 mmol) of IPDI, 91 g (0.045 mol) of UNIOL D-2000 (polypropylene glycol, manufactured by NOF Corporation, number average molecular weight of 2,000), 51.8 g of MEK, and 0.05 g of BHT were added thereto. While performing flushing with dry nitrogen, the temperature was raised to 70° C. After that, 10.4 mg of dibutyl tin dilaurate was added dropwise thereto. The reaction was carried out for 3 hours at 70° C. Next, 0.5 g (5 mmol) of HEA was added thereto. Under a dry air stream, the resulting product was continuously stirred for 3 hours while maintaining the temperature in the system at 80° C. The solvent was distilled off according to a reduced pressure method. As a viscous liquid, 103.6 g of UP-4 was obtained. In the same manner as Synthesis Example 1, according to an IR analysis, generation of a target reactive urethane polymer UP-4 was confirmed. The number average molecular weight of the obtained UP-4 was 68,000. Furthermore, the acryl equivalents was 22,500. Furthermore, the solution viscosity at 25° C. was found to be 1200 mPa·s.

The dissolution characteristics for general purpose organic solvents and acrylic monomers were evaluated by the following methods using the urethane modified (meth) acrylamide obtained in Synthesis Examples 1 to 7 and the urethane acrylic oligomer obtained in Comparative Synthesis Example 5, and the results are shown in Table 1.

Furthermore, the solvents and the monomers that are used in the evaluation are as follows.
IPA: isopropanol
MEK: methyl ethyl ketone
THF: tetrahydrofuran
"ACMO": N-acryloylmorpholine (registered trademark "ACMO")
HDDA: 1,6-hexanediol diacrylate
BA: butyl acrylate
IBOA: isobornyl acrylate
2EHA; 2-ethylhexyl acrylate
THFA; tetrahydrofurfuryl acrylate
(3) Solubility 1 part by weight of a general purpose solvent or an acrylic monomer was added to 1 part by weight of the obtained urethane modified (meth)acrylamide or the like. After stirring, the mixture was allowed to stand overnight. The extent of dissolution was examined by observation with a naked eye.

⊙: transparency was high, and cloudiness or separation was not observed at all.

○: transparency was high, but slight cloudiness was observed.

Δ: layer separation did not occur, but cloudiness was observed.

x: cloudiness was observed, and layer separation occurred.

As shown in the results of Evaluation examples and Comparative evaluation examples, the urethane acrylamide of an adduct type exhibited a poor solubility for general purpose organic solvents and acrylic monomers. In particular, the urethane acrylamide of an adduct type cannot be dissolved in a hydrophobic solvent and monomer. It cannot be handled as an active energy ray curable resin composition, and that is because the intramolecular and intermolecular hydrogen bond in the urethane acrylamide of an adduct type is very high. Dispersion in a solvent or a monomer of other type was difficult due to self aggregation.

By using the urethane modified (meth)acrylamide obtained in Synthesis Examples 1 to 6 and the urethane acrylic oligomer obtained in Comparative Synthesis Examples 1 to 4, an active energy ray curable resin composition was prepared. Then, by using those resin compositions, preparation of an ultraviolet ray cured film and evaluation of the cured film were carried out. The results are shown in Table 2.

Example A-1

100 parts by weight of the urethane modified (meth) acrylamide UY-1 obtained in Synthesis Example 1, 100 parts by weight of MEK, and 3 parts by weight of Darocur 1173 as a photopolymerization initiator were homogeneously mixed, and thus an active energy ray curable resin composition was prepared. Thereafter, using the obtained curable resin composition, an ultraviolet ray cured film was produced by the following method.

Method for Producing Ultraviolet Ray Cured Film

By applying to the anchor coat surface of a polyethylene terephthalate (PET) film ("Cosmoshine A4100" manufactured by Toyobo Co., Ltd., one side was anchor-coat-treated) having a thickness of 100 μm using a bar coater (RDS 12), a coating film was prepared such that the thickness of the dried coating film became 10 μm. The obtained coating film was dried at 80° C. for 2 minutes in an explosion-proof dryer, and cured by ultraviolet ray irradiation (apparatus: inverter type conveyor system ECS-4011GX manufactured by Eye Graphics Co., Ltd., metal halide lamp: M04-L41 manufactured by Eye Graphics Co., Ltd.), and thus an ultraviolet ray cured film was produced. The curing property of the resin composition was evaluated. Furthermore, the tack resistance, shrinkage resistance, transparency, water absorption rate, and adhesion property of the obtained cured film were evaluated by the following methods. The results are shown in Table 2.

(4) Curing Property

A dried coating film with thickness of 10 μm was prepared as described in the above. At a temperature of 70° C., ultraviolet ray irradiation was carried out for 120 seconds at illumination intensity of 2 mW/cm$^2$ (cumulative amount of light: 240 mJ/cm$^2$). The height of a peak derived from a vinyl group of the resin composition (1630 cm$^{-1}$) was measured by real time FT-IR. Accordingly, the curing rate of a coating film was calculated (Curing rate (%)=(Height of peak derived from vinyl group before curing−Height of peak derived from vinyl group after curing)/(Height of peak derived from vinyl group before curing×100).

⊙: curing rate of 90% or more
○: curing rate of 80% or more but less than 90%
Δ: curing rate of 50% or more but less than 80%
x: curing rate of less than 50%

(5) Tack Resistance

A dried coating film with thickness of 10 μm was prepared as described in the above. At a temperature of 70° C., ultraviolet ray irradiation was carried out for 3 seconds at illumination intensity of 700 mW/cm$^2$ (cumulative amount of light: 2100 mJ/cm$^2$). Accordingly, a completely cured coating film (completely cured film) was prepared. By touching the surface of a completely cured film with a finger, stickiness state was evaluated.

⊙: there was no stickiness at all.
○: although there was slight stickiness, a finger mark did not remain on the surface.
Δ: there was stickiness, and a finger mark remained on the surface.
x: stickiness was severe, and a finger stuck to the surface.

(6) Curl Resistance (Shrinkage Resistance)

A dried coating film with thickness of 60 μm was prepared as described in the above. The obtained completely cured film was cut into 10 cm square, and the floating height was measured at the four corners. The average value of the values measured with 5 pieces, which have been cut in the same manner as above, was calculated.

⊙: floating height was less than 0.5 mm.
○: floating height was 0.5 mm or more but less than 1 mm.
Δ: floating height was 1 mm or more but less than 3 mm.
x: floating height was 3 mm or more.

(7) Transparency (Naked Eye Observation)

The completely cured coating film obtained for the shrinkage resistance test described above was observed with a naked eye so that the transparency was evaluated.

⊙: it was transparent, and there was no opaqueness.
○: it was transparent, and there was slight opaqueness.
Δ: although there was opaqueness, transparent portions also remained.
x: there was severe opaqueness, and a transparent portion could not be confirmed.

(8) Water Absorption Rate

A curable resin composition was poured on a Teflon resin sheet which was hollowed such that the depth became 1 mm. After vacuum-drying (50° C., 400 torr), curing was performed by ultraviolet ray irradiation (700 mW/cm$^2$, 2,000 mJ/cm$^2$). Accordingly, an ultraviolet ray cured sheet was produced. The obtained sheet was cut into 3 cm square to obtain a test piece. The obtained test piece was allowed to stand in an environment of a temperature of 50° C. and a relative humidity of 95% for 24 hours, and then the water absorption rate was calculated (Water absorption rate (%)= (Weight after incubation at thermostatic and humidistatic conditions−Weight before incubation at thermostatic and humidistatic conditions)/Weight before incubation at thermostatic and humidistatic conditions×100)

(10) Adhesion Property

A completely cured film with thickness of 10 μm was prepared on top of a substrate formed of various materials as described in the above. Based on JIS K 5600, one hundred of squares of 1 mm×1 mm were created, and a cellophane tape was attached thereto. The evaluation was made by counting the number of squares in which the coating film remained on the substrate side when the tape was peeled all at once.

Examples A-2 to A-7 and Comparative Examples A-8 to A-11

An ultraviolet ray curable resin composition was prepared in the same manner as Example A-1 except that the composition described in Table 2 is used instead. A cured film was also prepared. The evaluation was made based on the methods described above. The results are shown in Table 2.

As shown in the results of the Evaluation examples and the Comparative evaluation examples, the urethane modified (meth)acrylamide of the present invention has a high active energy ray curing property as it has a molecular weight and acryl equivalents that are within the specific range. Furthermore, the obtained cured film has favorable surface dryness (tack resistance), curl resistance, and water resistance. Transparency and adhesion property to various substrates are also satisfied. However, once the molecular weight and acryl equivalents are outside the specific range of the present invention, it is impossible to obtain an cured film capable of satisfying all of the curing property, tack resistance, and curl resistance. As a result, the transparency, adhesion property, and water resistance of the cured film were also deteriorated. When the molecular weight is excessively high, in particular, the characteristics originating from the carbonate skeleton and ether skeleton are strongly exhibited. As a result, the transparency accompanying the improved crystallinity was deteriorated. In addition, a decrease in the adhesion property of a cured film (Comparative Evaluation Example A-8) or sticking on a surface of cured film (Comparative Evaluation Example A-9) became significant.

Meanwhile, with the urethane acrylic oligomer containing (meth)acrylate, one or more performances of the curing property, tack resistance, and curl resistance were not satisfied even when the molecular weight and acryl equivalents are all within the specific range of the present invention. The adhesion property was also low. Meanwhile, favorable outer-looking tack resistance was shown from Comparative Evaluation Example A-11 in which 6 acrylate groups are contained per molecule. However, the curing rate of a vinyl group was less than 50%. Furthermore, the curing shrinkage rate was also high.

The urethane modified (meth)acrylamide of the present invention has a molecular weight and acryl equivalents that are within the specific range, and also has a high curing property. In spite of such feature, it was possible to obtain a cured film with excellent curl resistance. In this regard, it is assumed by the inventors of the present invention as follows. Namely, as the hydrogen bond between amide groups or between an amide group and a urethane bond is strong, the urethane modified (meth)acrylamide of the present invention remains in an aggregated state even before curing. As a result, the intermolecular distance is not likely to decrease significantly before and after curing. Due to such reasons, the shrinkage property of the entire cured film can be suppressed, too.

The characteristics evaluation in each field of application was performed by using the urethane modified (meth)acrylamide obtained in Synthesis Examples 1 to 7 and the urethane acrylic oligomer obtained in Comparative Synthesis Examples 1 to 5. The materials used in Examples and the Comparative examples are as follows.

"HEAA"; hydroxyethyl acrylamide (manufactured by KJ Chemicals Corporation) "DMAA"; N,N-dimethyl acrylamide (manufactured by KJ Chemicals Corporation) "DEAA"; N,N-diethyl acrylamide (manufactured by KJ Chemicals Corporation) "ACMO"; N-acryloylmorpholine (manufactured by KJ Chemicals Corporation) "DMAPAA"; dimethylaminopropyl acrylamide (manufactured by KJ Chemicals Corporation)

HEA; hydroxyethyl acrylate
2EHA; 2-ethylhexyl acrylate
EEA; 2-(2-ethoxyethoxy)ethyl acrylate
THFA; tetrahydrofurfuryl acrylate
IBOA; isobornyl acrylate
IBMA; isobornyl methacrylate
VEEA; 2-(2-vinyloxyethoxy)ethyl acrylate
CHA; cyclohexyl acrylate
CHMA; cyclohexyl methacrylate
4HBA; 4-hydroxybutyl acrylate
A-LEN-10; ethoxyated-o-phenylphenol acrylate (manufactured by Shin Nakamura Chemical Co., Ltd.)
HDDA; 1,6-hexane diol diacrylate
TPGDA; tripropylene glycol diacrylate
PETA; pentaerythritol triacrylate
DPHA; dipentaerythritol hexaacrylate
DMAEA-TFSIQ; acryloyloxyethyltrimethylammonium bis(trifluoromethanesulfonyl)imide (manufactured by KJ Chemicals Corporation) DMAPAA-TFSIQ; acryloylaminopropyltrimethylammonium bis(trifluoromethanesulfonyl)imide (manufactured by KJ Chemicals Corporation)
Irgacure 184; 1-hydroxy-cyclohexyl-phenyl-ketone (manufactured by BASF Japan Ltd.)
Irgacure 1173; 2-hydroxy-2-methyl-1-phenyl-propan-1-one (manufactured by BASF Japan Ltd.)
Irgacure TPO; 2,4,6-trimethylbenzoyl-diphenyl-phosphine oxide (manufactured by BASF Japan Ltd.)
Irgacure 819; bis(2,4,6-trimethylbenzoyl)-phenyl phosphine oxide (manufactured by BASF Japan Ltd.)
Irgacure 127; 2-hydroxy-1-[4-[4-(2-hydroxy-2-methyl-propionyl)benzyl]phenyl]-2-methyl-propan-1-one (manufactured by BASF Japan Ltd.)
Hitaroid 7851; epoxyacrylate oligomer (manufactured by Hitachi Chemical Co., Ltd.).
Hitaroid 7975; acryl acrylate oligomer (manufactured by Hitachi Chemical Co., Ltd.) (as a solvent type material, it was used after removing the solvent using an evaporator).

Evaluation Example B-1

8 parts by weight of the urethane modified (meth)acrylamide UY-1 synthesized in Synthesis Example 1, 30 parts by weight of the reactive urethane polymer UP-4 synthesized in Synthesis Example 12, 10 parts by weight of "HEAA", 30 parts by weight of "DEAA", 4 parts by weight of CHA, 15 parts by weight of EEA, and 3 parts by weight of DMAPAA-TFSIQ were admixed with one another. Then, 1 part by weight of Irgacure 184 as a photopolymerization initiator was added thereto, and the resulting product was homogeneously mixed, and thus an ultraviolet ray curable cohesive was prepared. Thereafter, using the obtained cohesive, a cohesive sheet was produced by ultraviolet ray curing according to the following method, and evaluation thereof was performed.

Method for Producing Ultraviolet Ray Curing Type Cohesive Sheet

The ultraviolet ray curing type cohesive prepared in the above was applied to a heavy peeling separator (silicone coated PET film), then, using a desktop type roll laminator (RSL-382S manufactured by Royal Sovereign), a light peeling separator (silicone coated PET film) was attached thereto such that the thickness of the cohesive layer became 25 μm and air bubbles were not to be entrapped, and irradiation (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm$^2$, cumulative amount of light: 2,000 mJ/cm$^2$) with ultraviolet rays was performed, and thus an optical transparent cohesive sheet was prepared. The characteristics of the obtained cohesive sheet were evaluated by the following methods. The results are shown in Table 3.

(10) Transparency (Transmittance)

Under conditions of a temperature of 23° C. and a relative humidity of 50%, the surface from which the light peeling separator had been peeled, of the cohesive sheet cut into a shape with a width of 25 mm was attached to a glass substrate as an adherend, then, a heavy peeling separator was peeled, and the transmittance was measured. After the total light transmittance of the glass substrate was measured using a haze meter (NDH-2000 manufactured by Nippon Denshoku Industries Co., Ltd.) according to JIS K 7105, by subtracting the transmittance of the glass plate, the transmittance of the cohesive layer itself was calculated, and the transparency was evaluated. As the transmittance was higher, the transparency was better.

(11) Measurement of Surface Resistivity

Using a template (height 110×width 110 mm), the cohesive sheet was cut with a cutter knife, and the cut cohesive sheets were put in a thermostatic and humidistatic apparatus adjusted to a temperature of 23° C. and a relative humidity of 50% and allowed to stand for 3 hours, and thus a sample for surface resistivity measurement was obtained. The surface resistivity was measured using a digital electrometer (R8252 type: manufactured by ADC CORPORATION) according to JIS K 6911.

(12) Cohesive Force

Under conditions of a temperature of 23° C. and a relative humidity of 50%, transfer, to a polyethylene terephthalate (PET) film (thickness of 100 μm) or a glass substrate as an adherend was carried out. After that, by reciprocally moving two times a pressure roller of a load of 2 kg, pressure-attachment was performed, and the resulting product was allowed to stand for 30 minutes in the same environment. Thereafter, using a tension tester (apparatus name: Tensilon RTA-100 manufactured by ORIENTEC Co., Ltd.), the 180° peeling resistance (N/25 mm) was measured at a peeling rate of 300 mm/min.

⊙: 15 (N/25 mm) or higher.
○: 10 (N/25 mm) or higher but lower than 15 (N/25 mm).
Δ: 3 (N/25 mm) or higher but lower than 10 (N/25 mm).
x: lower than 3 (N/25 mm)

(13) Contamination Resistance

A cohesive sheet was attached to an adherend in the same manner as in the measurement of cohesive force described above, then, the resulting product was allowed to stand at 80° C. for 24 hours, and contamination of the adherend surface after the cohesive sheet was peeled was observed with a naked eye.

⊚: there is no contamination.
○: there is very slight contamination.
Δ: there is slight contamination.
x: there are glue (cohesive) residues.

(14) Yellowing Resistance

A cohesive sheet was attached to a glass substrate, then, the resultant was set to a xenon fade meter (SC-700-WA: manufactured by Suga Test Instruments Co., Ltd.), and after irradiation with ultraviolet rays was performed at an intensity of 70 mW/cm$^2$ for 120 hours, the color change of the cohesive sheet was observed with a naked eye.

⊚: yellowing cannot be observed with a naked eye at all.
○: very slight yellowing can be observed with a naked eye.
Δ: yellowing can be observed with a naked eye.
x: obvious yellowing can be observed with a naked eye.

(15) Moisture and Heat Resistance

A cohesive sheet was attached to a glass substrate in the same manner as in the yellowing resistance test described above, and kept for 100 hours under conditions of a temperature of 85° C. and a relative humidity of 85%. After that, an occurrence of floating, peeling, bubbles, or cloudiness was observed with a naked eye, and based on that, evaluation was performed.

⊚: it is transparent, and floating/peeling and bubble do not occur.
○: although there is very slight opaqueness, floating/peeling and bubble do not occur.
Δ: there are slight opaqueness or floating/peeling, and bubbles.
x: there are severe opaqueness or floating/peeling, and bubbles.

(16) Step Followability

A black tape having a thickness of 20 μm was attached to a glass substrate, and thus a stepped glass was produced. After a cohesive sheet was transferred to the stepped glass, by reciprocating once (pressing speed of 300 mm/min) using a roller of a load of 2 kg on the sheet surface in an environment of a temperature of 23° C. and a relative humidity of 50%, pressure-attachment was performed, then, the resulting product was allowed to stand at a temperature of 80° C. for 24 hours, and the state of the stepped portion was observed using an optical microscope.

⊚: bubbles are not observed at all.
○: slightly small spherical bubbles are observed.
Δ: large bubbles are observed, and there is a case where bubbles are connected to each other.
x: large bubbles are connected to each other, and spread on the line in the stepped portion.

(17) Punching Processability

The obtained cohesive sheet was cut by a Thompson punching method (punching method by punching blades, in which 10 linear blades were arranged at 5.0 mm intervals in parallel).

⊚: nothing remains on the punching blades.
○: slight cohesive remains on the punching blades.
Δ: cohesive remains on the punching blades.
x: cohesive significantly remains on the punching blades, and cutting surface cannot be clearly observed.

Evaluation Examples B-2 to 7 and Comparative Evaluation Examples B-8 to 11

An ultraviolet ray curable resin composition was prepared in the same manner as Evaluation Example B-1 except that the composition described in Table 3 is used instead. A cohesive sheet was also prepared. The evaluation was made based on the methods described above. The results are shown in Table 3.

As shown in the results of the Evaluation examples and the Comparative evaluation examples, it was found that the cohesive force and moisture and heat resistance tend to decrease when the urethane modified (meth)acrylamide which has a molecular weight and acryl equivalents that are outside the specific range, or the urethane modified (meth)acrylate which has a molecular weight and acryl equivalents that are within the specific range is blended. Furthermore, the contamination resistance and punching processability of a cohesive sheet after curing were poor. Thus, it is difficult to be used in view of such aspect. By using the urethane modified (meth)acrylamide of the present invention, a cohesive sheet excellent in contamination resistance and punching processability can be obtained while having the transparency and cohesive force.

Evaluation Example C-1

22 parts by weight of the urethane modified (meth)acrylamide UY-1 synthesized in Synthesis Example 1, 15 parts by weight of the reactive urethane polymer UP-3 synthesized in Synthesis Example 10, 18 parts by weight of "ACMO", 9 parts by weight of "HEAA", 14 parts by weight of "DMAA", 10 parts by weight of THFA, and 12 parts by weight of IBOA were admixed with one another. Then, 3 parts by weight of Irgacure 1173 as a photopolymerization initiator was added thereto, and the resulting product was homogeneously mixed, and thus an ultraviolet ray curable cohesive was prepared. Thereafter, by using the obtained cohesive, a polarizing plate was produced by ultraviolet ray curing by the following method, and the physical properties of the polarizing plate were evaluated.

Production of Polarizing Plate by UV Irradiation

Using a desktop type roll laminator (RSL-382S manufactured by Royal Sovereign), a polarizing film was sandwiched between two sheets of transparent films (protective film, phase difference film or optical compensation film), and the adhesive of the example or the comparative example was applied between the transparent film and the polarizing film such that the thickness became 10 μm. By performing irradiation (ultraviolet illumination intensity: 700 mW/cm$^2$, cumulative amount of light: 2,000 mJ/cm$^2$) with ultraviolet rays from the upper surface of the attached transparent film, a polarizing plate having a transparent film on both sides of the polarizing film was produced.

(18) Observation of Surface Shape

The surface of the obtained polarizing plate was observed with a naked eye, and evaluation was performed according to the following criteria.

⊚: fine streaks and irregularity cannot be observed on the surface of the polarizing plate.
○: fine streaks can be partly observed on the surface of the polarizing plate.
Δ: fine streaks or irregularity can be observed on the surface of the polarizing plate.
x: obvious streaks or irregularity can be observed on the surface of the polarizing plate

(19) Peeling Strength

Under conditions of a temperature of 23° C. and a relative humidity of 50%, a polarizing plate (test piece) cut into 20 mm×150 mm was attached to a test plate attached to a tension tester (Autouaph AGXS-X 500N manufactured by Shimadzu Corporation) with a double-sided adhesive tape. A piece of transparent protective film and polarizing film on the side which was not attached with a double-sided adhesive tape was peeled at about 20 to 30 mm in advance and secured to an upper clamping tool, and the 90° peeling strength (N/25 mm) was measured at a peeling rate of 300 mm/min.

⊙: 3.0 (N/25 m) or greater.
○: 1.5 (N/25 m) or greater but less than 3.0 (N/25 m).
Δ: 0.5 (N/25 m) or greater but less than 1.5 (N/25 m).
x: less than 0.5 (N/25 m).

(20) Water Resistance

The obtained polarizing plate was cut into 20×80 mm, then, it was soaked in warm water at 60° C. for 48 hours, and the presence or absence of peeling at the interfaces between the polarizer and the protective film, the phase difference film, and the optical compensation film was observed. Determination was performed according to the following criteria.

⊙: there is no peeling at the interface between the polarizer and the protective film (less than 1 mm).
○: there is peeling at a part of the interface between the polarizer and the protective film (1 mm or greater but less than 3 mm).
Δ: there is peeling at a part of the interface between the polarizer and the protective film (3 mm or greater but less than 5 mm).
x: there is peeling at the interface between the polarizer and the protective film (5 mm or greater).

(21) Durability

After the obtained polarizing plate was cut into 150 mm×150 mm, the cut polarizing plate was put into a thermal shock apparatus (TSA-101 L-A manufactured by ESPEC CORP.), then, heat shock at −40° C. to 80° C. was performed 100 times for 30 minutes, respectively, and evaluation was carried out according to the following criteria.

⊙: cracks do not occur.
○: short cracks of 5 mm or smaller occur only at the ends.
Δ: cracks occur in a short linear shape at places other than the ends, but the polarizing plate is not separated into two or more portions by that line.
x: cracks occur at places other than the ends, and by the line, the polarizing plate is separated into two or more portions.

Evaluation Examples C-2 to 7 and Comparative Evaluation Examples C-8 to 11

An ultraviolet ray curable resin was prepared in the same manner as Evaluation Example C-1 except that the composition described in Table 4 is used instead. A polarizing plate was also prepared. The evaluation was made based on the methods described above. The results are shown in Table 4.

As shown in the results of the Evaluation examples and the Comparative evaluation examples, it was found that the flexibility originating from the main skeleton such as ether or ester tends to increase when the urethane modified (meth)acrylamide which has a molecular weight and acryl equivalents that are outside the specific range, or the urethane modified (meth)acrylate which has a molecular weight and acryl equivalents that are within the specific range is blended. Furthermore, the peeling strength and water resistance tend to decrease. Furthermore, due to incomplete curing of the adhesive, lower peeling strength and durability were caused. Thus, it is difficult to be used in view of such aspect. The adhesive using the urethane modified (meth) acrylamide of the present invention has high cross-linking density. Accordingly, it was found to have high peeling strength and durability, good balance between the flexibility and strength, and also excellent water resistance.

Evaluation Example D-1

48 parts by weight of the urethane modified (meth) acrylamide UY-1 synthesized in Synthesis Example 1, 15 parts by weight of HDDA, 24 parts by weight of TPGDA, 8 parts by weight of "DEAA", 5 parts by weight of IBOA, 3 parts by weight of a pigment and 3 parts by weight of a pigment dispersing agent were admixed with one another. Then, 2 parts by weight of Irgacure 819 and 3 parts by weight of Irgacure 127 as a photopolymerization initiator were added thereto, and the resulting product was homogeneously mixed, and thus a photocurable ink composition was prepared. Thereafter, ink jet printing was performed by the following method, and evaluation of the obtained printed matter was performed.

(22) Viscosity

The viscosity of the obtained ink composition was measured by using a cone-plate type viscometer (apparatus name: RE550 viscometer manufactured by Toki Sangyo Co., Ltd.) according to JIS K5600-2-3. Based on ink jet type printing, the viscosity of the ink composition at 20° C. is preferably 3 to 20 mPa·s, and more preferably 5 to 18 mPa·s. If the viscosity is less than 3 mPa·s, print smearing after discharge and reduction of discharge followability by printing deviation are seen, and if the viscosity is 20 mPa·s or greater, reduction of discharge stability due to clogging of discharge nozzles is seen. Due to such reasons, viscosity of 20 mPa·s or greater is not desirable.

(23) Compatibility

The compatibility of the ink composition prepared by the above method was observed with a naked eye.

⊙: an insoluble material is not observed in the ink composition.
○: slight insoluble materials are observed in the ink composition.
Δ: insoluble materials are observed over the entire ink composition.
x: precipitates are observed in the ink composition.

Production of Printed Matter by UV Irradiation

The obtained ink composition was applied using a bar coater (RDS 12) onto a polyethylene terephthalate (PET) film having a thickness of 100 μm. According to curing by ultraviolet ray irradiation (apparatus LED type UV irradiation system H-10MAH20-1T18, manufactured by HOYA, 385 nm), a printed matter was produced.

(24) Curing Property

When a printed matter was produced by the above method, under an environment with room temperature of 23° C., the cumulative amount of light required to have complete curing of the ink composition was measured.

⊙: completely cured at 500 mJ/cm$^2$
○: completely cured at 500 to 1000 mJ/cm$^2$
Δ: completely cured at 1000 to 2000 mJ/cm$^2$
x: 2000 mJ/cm$^2$ or higher is required to have complete curing.

(25) Surface Dryness

After the printed matter produced by the above method was allowed to stand in an environment of a temperature of 23° C. and a relative humidity of 50% for 5 minutes, high quality paper was superimposed on the printed surface, then, a load of 1 kg/cm² was applied thereto over a period of 1 minute, and the degree of transfer of ink to the paper was evaluated.
⊙: ink was dried, and transfer to the paper did not occur at all.
○: ink was dried, and slight transfer to the paper occurred.
Δ: ink was nearly dried, and transfer to the paper occurred.
x: ink was hardly dried, and significant transfer to the paper occurred.
Inkjet Printing and Printability Evaluation A solid image was printed using an ink jet type color printer (PM-A890 manufactured by Seiko Epson Corporation); and by performing irradiation with ultraviolet rays (ultraviolet illumination intensity: 700 mW/cm², cumulative amount of light of 2,000 mJ/cm²), a printed matter was produced, and evaluation was performed by the following method. The results are shown in Table 5.
(26) Discharge Stability Printing was performed using the inkjet printer described above, and the print state of the printed matter was evaluated with a naked eye.
⊙: there was no nozzle absence, and it was well printed.
○: there was slight nozzle absence.
Δ: there was nozzle absence over a wide range.
x: there was no discharge.
(27) Sharpness The sharpness of an image after printing was observed with a naked eye.
⊙: ink smearing was not observed at all, and the image was sharp.
○: ink smearing was almost not observed, and the image was good.
Δ: slight ink smearing was observed.
x: significant ink smearing was observed.
(28) Water Resistance The printed surface was exposed to flowing water for 1 minute, and the change in the image was observed with a naked eye.
⊙: the sharpness of the image was not changed at all.
○: although the sharpness of the image was almost not changed, slight ink smearing was observed.
Δ: the sharpness of the image was lowered, and ink smearing was observed.
x: the sharpness of the image was significantly lowered, and significant smearing was observed.

Evaluation Examples D-2 to 7 and Comparative Evaluation Examples D-8 to 11

An ink composition was prepared in the same manner as Evaluation Example D-1 except that the composition described in Table 5 is used instead. A printed matter was also prepared according to the aforementioned method. The evaluation was made based on the methods described above. The results are shown in Table 5.

As shown in the results of the Evaluation examples and the Comparative evaluation examples, it was found to have high viscosity after preparing an ink composition when the urethane modified (meth)acrylamide which has a molecular weight and acryl equivalents that are outside the specific range, or the urethane modified (meth)acrylate which has a molecular weight and acryl equivalents that are within the specific range is blended. Accordingly, a tendency of having lower discharge stability, curing property, and surface dryness was found. Furthermore, due to the sticking originating from the main skeleton and low curing property of (meth) acrylate, smearing in a printer matter was shown after discharge curing. When the urethane modified (meth)acrylamide of the present invention is used, it was able to obtain an ink composition which has a high curing property and curing density, as well as surface dryness, sharpness, and water resistance.

Evaluation Example E-1

15 parts by weight of the urethane modified (meth) acrylamide UY-1 synthesized in Synthesis Example 1, 20 parts by weight of the reactive urethane polymer UP-1 synthesized in Synthesis Example 8, 30 parts by weight of the reactive urethane polymer UP-3 synthesized in Synthesis Example 10, 25 parts by weight of PETA, and 10 parts by weight of IBOA were admixed with one another. Then, 3 parts by weight of Darocur 1173 as a photopolymerization initiator was added thereto, and the resulting product was homogeneously mixed, and thus a photocurable coating composition was prepared.
(29) Compatibility The compatibility of the coating agent composition obtained by the above method was observed with a naked eye.
⊙: transparency of the coating composition is high, and cloudiness or separation is not observed at all.
○: although transparency of the coating composition is high, slight cloudiness is observed.
Δ: cloudiness is observed over the entire coating composition.
c: cloudiness of the coating composition is observed, and separation occurs.
(30) Wettability The obtained coating agent composition was applied to a substrate, and the adhered state of the coating film was observed with a naked eye.
⊙: even immediately after applying, or after being allowed to stand for 5 minutes, a smooth coating film was formed with no floating.
○: there was no floating immediately after application, but after being allowed to stand for 5 minutes, slight floating was observed.
Δ: slight floating was observed immediately after application.
x: significant floating was observed immediately after application, and a uniform coating film was not obtained.
Production of Coating Film by Ultraviolet Ray Irradiation The obtained coating agent composition was applied to a PET film having a thickness of 100 μm using a bar coater (RDS 12). By performing irradiation (ultraviolet illumination intensity: 700 mW/cm²) with ultraviolet rays, a coating film (thickness of 10 μm) was produced, and evaluation was performed on the coating film by the following method. The results are shown in Table 6. In a case where a solvent was used, ultraviolet ray irradiation was performed after drying at 80° C. for 3 minutes after coating.
(31) Curing Property The coating agent composition was applied, then, the obtained coating film was irradiated with ultraviolet rays of ultraviolet ray illumination of 700 mW/cm² under an environment with room temperature of 23° C., and the cumulative amount of light required to have complete curing of the resin composition was measured. The complete cure means a state in which, when the surface of the cured film is rubbed with silicone rubber, there is no trace.
⊙: completely cured at a cumulative amount of light of 1,000 mJ/cm².

○: completely cured at a cumulative amount of light of 1,000 mJ/cm² to 2,000 mJ/cm².
Δ: completely cured at a cumulative amount of light of 2,000 mJ/cm² to 5,000 mJ/cm².
x: a cumulative amount of light of 5,000 mJ/cm² or greater is required until completely cures.
(32) Tack Resistance The surface of the coating film obtained by the above method was touched with a finger, and the degree of stickiness was evaluated.
⊙: there is no stickiness.
○: although there is slight stickiness, a finger mark does not remain on the surface.
Δ: there is stickiness, and a finger mark remains on the surface.
x: stickiness is strong, and a finger sticks to the surface.
(33) Curl Resistance (Shrinkage Resistance)

A coating film obtained by irradiating the coating film obtained by the above method with ultraviolet rays (ultraviolet illumination intensity of 700 mW/cm², cumulative amount of light of 2,000 mJ/cm²) was cut into 10 cm square, and the average of floating of the four corners was measured.
⊙: floating height was less than 0.5 mm.
○: floating height was 0.5 mm or more but less than 1 mm.
Δ: floating height was 1 mm or more but less than 3 mm.
x: floating height was 3 mm or more.
(34) Scratch Resistance Steel wool of #0000 was reciprocally moved ten times while a load of 200 g/cm² was applied, and the presence of an occurrence of scratches was evaluated with a naked eye.
⊙: peeling of a film and occurrence of scratches are hardly observed.
○: fine scratches are slightly observed on a part of a film.
Δ: streaky scratches are observed on the entire film surface.
x: peeling of a film occurs.
(35) Self Restoring Property The coating film obtained by the above method was scratched using a spoon and allowed to stand in an environment of a temperature of 25° C. and a relative humidity of 50%, and the recovery state from scratches was evaluated with a naked eye.
⊙: scratches are completely recovered within 30 minutes.
○: scratches are completely recovered within 30 minutes to 5 hours.
Δ: scratches are completely recovered within 5 hours to 24 hours.
x: scratches are not completely recovered even after being allowed to stand for 24 hours.
(36) Adhesion Property According to JIS K 5600, one hundred of squares of 1 mm×1 mm were created, then, a cellophane tape was attached thereto, and evaluation was performed by counting the number of squares in which the coating film remained on the substrate side when the tape was peeled all at once.
(37) Moisture Resistance The coating film obtained on a PET film (100 vim) was allowed to stand in an environment of a temperature of 50° C. and a relative humidity of 95% for 24 hours, and the subsequent film was evaluated with a naked eye or by an adhesion property test.
⊙: transparency is maintained at high temperature and high humidity, and deterioration of adhesion property is not observed.
○: although transparency is maintained at high temperature and high humidity, slight deterioration of adhesion property is observed.
Δ: although transparency is maintained at high temperature and high humidity, significant deterioration of adhesion property is observed.
x: deterioration of transparency at high temperature and high humidity or deterioration of adhesion property is observed.

Evaluation Examples E-2 to 7 and Comparative Evaluation Examples E-8 to 11

A coating composition was prepared in the same manner as Evaluation Example E-1 except that the composition described in Table 6 is used instead. A cured film was also prepared according to the above method. The evaluation was made based on the methods described above. The results are shown in Table 6.

As shown in the results of the Evaluation examples and the Comparative evaluation examples, a tendency of having lower curing property of the coating agent and lower surface dryness (tack resistance) of the obtained coating film, and lower scratch resistance and self restoring property was confirmed when the urethane modified (meth)acrylamide which has a molecular weight and acryl equivalents that are outside the specific range, or the urethane modified (meth) acrylate which has a molecular weight and acryl equivalents that are within the specific range is blended. When the urethane modified (meth)acrylamide of the present invention is used, the crosslinking density inside the cured film was high. Accordingly, it was possible to prepare a cured film having scratch resistance and self restoring property, in addition to the curing property and surface dryness.

Evaluation Example F-1

32 parts by weight of the urethane modified (meth) acrylamide UY-1 synthesized in Synthesis Example 1, 5 parts by weight of the urethane modified (meth)acrylamide UY-6 synthesized in Synthesis Example 6, 22 parts by weight of the reactive urethane polymer UP-2 synthesized in Synthesis Example 9, 5 parts by weight of "ACMO", 21 parts by weight of IBMA, and 15 parts by weight of CHMA were admixed with one another. Then, 3 parts by weight of Irgacure 184 as a photopolymerization initiator was added thereto, and the resulting product was homogeneously mixed, and thus a coating agent composition for finger nail decoration was prepared.
Method for Finger Nail Decoration The obtained coating agent composition for finger nail decoration was evenly applied on top of a finger nail by using a flat brush. According to irradiation with an LED light (12 W), which is exclusively used for gel nail, for 20 seconds, finger nail decoration was formed on top of a finger nail.
(38) Curing Property By touching the surface of the finger nail decoration which has been obtained by the above method with a finger, sticking state was evaluated.
⊙: there is no stickiness at all.
○: although there is slight stickiness, a finger mark does not remain on the surface.
Δ: there is stickiness, and a finger mark remains on the surface.
x: stickiness is severe, and a finger sticks to the surface.
(39) Smoothness The surface of the finger nail decoration which has been obtained by the above method was observed with a naked eye.

⊙: surface is smooth, and no irregularities are observed from any part of the coated surface.
○: overall smoothness is observed, but some irregularities are observed.
Δ: brush marks of a flat brush partially remain after the application.
x: brush marks of a flat brush remain after the application.
(40) Glossiness The surface of the finger nail decoration which has been obtained by the above was observed with a naked eye.
⊙: there is surface glossiness.
○: light reflection can be confirmed, but slight opaqueness is shown.
Δ: overall, surface is slightly opaque.
x: surface is opaque.
(41) Adhesion Property The finger nail decoration which has been obtained by the above was scratched with other finger nail. Thereafter, a change in the outer appearance in the finger nail decoration was determined with a naked eye.
⊙: there is no change in the outer appearance.
○: slight floating is shown in part of the finger nail decoration, and whitening is found.
Δ: peeling is found from part of the finger nail decoration.
x: significant peeling of the finger nail decoration is found.
(42) Removability Cotton containing acetone was applied such that it can cover the finger nail decoration which has been obtained by the above method. Next, after wearing saniment gloves, the finger nail fully covered with aluminum foil was allowed to be immersed in hot water for 10 minutes. After removing the aluminum foil and cotton, the finger nail was briefly rubbed by using cloth.
⊙: finger nail decoration can be easily peeled even without using the cloth.
○: finger nail decoration can be easily peeled when gentle rubbing using cloth is carried out.
Δ: finger nail decoration can be peeled when rubbing is continued for 1 minute or so by using cloth.
x: acetone swelling does not occur, and peeling cannot be achieved even after rubbing with cloth.

Evaluation Examples F-2 to 7 and Comparative Evaluation Examples F-8 to 11

A coating agent composition for finger nail decoration was prepared in the same manner as Evaluation Example F-1 except that the composition described in Table 7 is used instead. Furthermore finger nail decoration was made according to the methods described above. The evaluation was made based on the methods described above. The results are shown in Table 7.

As shown in the results of the Evaluation examples and the Comparative evaluation examples, the following tendency was shown when the urethane modified (meth)acrylamide which has a molecular weight and acryl equivalents that are outside the specific range, or the urethane modified (meth)acrylate which has a molecular weight and acryl equivalents that are within the specific range is blended. Namely, the curing property of the composition and the glossiness of the obtained decorated film were poor. Furthermore, the flexibility and stickiness originating from the main skeleton are yielded. For such reasons, poor smoothness is caused at the time of forming finger nail decorations on finger nails. Furthermore, liquid flow and brush mark of a flat brush remain. When the urethane modified (meth) acrylamide of the present invention is used, sticking of a decorated film after curing is suppressed.

Furthermore, floating from a finger nail is low during curing. Due to such reasons, there is also no floating from a finger nail. As such, it was possible to form a finger nail decoration which has not only the high adhesion property but also high removability with acetone.

Evaluation Example G-1

24 parts by weight of the urethane modified (meth) acrylamide UY-1 synthesized in Synthesis Example 1, 12 parts by weight of the urethane modified (meth)acrylamide UY-2 synthesized in Synthesis Example 2, 25 parts by weight of the urethane polymer UP-1 synthesized in Synthesis Example 8, 5 parts by weight of the reactive urethane polymer UP-2 synthesized in Synthesis Example 9, 10 parts by weight of "ACMO", 4 parts by weight of "DEAR", 10 parts by weight of 4-HBA, and 10 parts by weight of A-LEN-10 were admixed with one another. Then, 2 parts by weight of Irgcure 184 and 2 parts by weight of Irgacure TPO as a photopolymerization initiator were added thereto, and the resulting product was homogeneously mixed, and thus a photocurable sealing agent was prepared.
Method for Producing Cured Product of Photocuring Type Sealing Agent Resin A silicon spacer (height 30 mm×width 15 mm×thickness 3 mm) was set on a glass plate (height 50 mm×width 50 mm×thickness 5 mm), and the photocuring type sealing agent prepared above was injected to the inside of the spacer. After thorough deaeration, by performing irradiation with ultraviolet rays (ultraviolet illumination intensity: 700 mW/cm$^2$, cumulative amount of light: 2,000 mJ/cm$^2$), a cured product of a sealing agent resin was produced. The characteristics of the obtained cured product were evaluated by the following methods. The results are shown in Table 8.
(43) Transparency The obtained cured product was allowed to stand in an environment of a temperature of 23° C. and a relative humidity of 50% for 24 hours. Thereafter, the transmittance of the cured film was measured using a haze meter (NDH-2000 manufactured by Nippon Denshoku Industries Co., Ltd.), and the transparency was evaluated on a scale of four levels that are described below.
⊙: transmittance is 90% or greater.
○: transmittance is 85% or greater but less than 90%.
Δ: transmittance is 50% or greater but less than 85%.
x: transmittance is less than 50%.
(44) Light Resistance The obtained cured product was attached to a glass substrate, and the degree of yellowing was measured by using a spectrophotometer (CM-3600d manufactured by Konica Minolta, Inc.). Thereafter, the cured product was set to a xenon fade meter (SC-700-WA, manufactured by Suga Test Instruments Co., Ltd.), and after irradiation with ultraviolet rays was performed at an intensity of 4 W/cm$^2$ at 30° C. for 100 hours, the degree of yellowing after the irradiation was measured in the same manner as before the irradiation, and the color change of the cured product was observed with a naked eye.
⊙: yellowing cannot be observed at all with a naked eye.
○: very slight yellowing can be observed with a naked eye.
Δ: yellowing can be observed with a naked eye.
x: obvious yellowing can be observed with a naked eye.
(45) Water Resistance 1 g of a test specimen was taken from the obtained cured product, set in a thermostatic and humidistatic apparatus of a temperature 85° C. and a relative humidity of 95%, and allowed to stand for 48 hours, then, the test piece was weighed again, and the water absorption rate was calculated (Water absorption rate (%)=(Weight after incubation at thermostatic and humidistatic conditions−Weight before incubation at thermostatic and humidistatic conditions)/Weight before incubation at thermostatic and humidistatic conditions×100)

⊙: water absorption rate is less than 1.0%
◯: water absorption rate is 1.0% or greater but less than 2.0%
Δ: water absorption rate is 2.0% or greater but less than 3.0%
x: water absorption rate is 3.0% or greater

(46) Out Gas Test 1 g of a test specimen was taken from the obtained cured product. The test specimen was then allowed to stand in a thermostat set to a temperature of 100° C., dry nitrogen was flowed thereto for 24 hours, then, the test piece was weighed again, and the outgas generation rate was calculated (Out gas generation rate (%)=(Weight after incubation at thermostatic conditions−Weight before incubation at thermostatic conditions)/Weight before incubation at thermostatic conditions×100)

⊙: generation rate is less than 0.1%
◯: generation rate is 0.1% or greater but less than 0.3%
Δ: generation rate is 0.3% or greater but less than 1.0%
x: generation rate is 1.0% or greater

(47) Heat cycle resistance

One cycle in which the obtained cured product was allowed to stand at −40° C. for 30 minutes, and then at 100° C. for 30 minutes was repeated 10 times, and the state of the cured product was observed with a naked eye.

⊙: change is not observed at all
◯: although bubbles slightly occur, occurrence of cracks is not observed, and it is transparent.
Δ: occurrence of some of bubbles or cracks is observed, and there is slight opaqueness.
x: bubbles or cracks fully occur, and it is a semi-transparent state.

Evaluation Examples G-2 to 7 and Comparative Evaluation Examples G-8 to 12

An ultraviolet ray curable resin was further prepared in the same manner as Evaluation Example G-1 except that the composition described in Table 8 is used instead. Furthermore, a cured product of a sealing agent was prepared. The evaluation was made based on the methods described above. The results are shown in Table 8.

As shown in the results of the Evaluation examples and the Comparative evaluation examples, the following tendency was shown when the urethane modified (meth)acrylamide which has a molecular weight and acryl equivalents that are outside the specific range, or the urethane modified (meth)acrylate which has a molecular weight and acryl equivalents that are within the specific range is blended. Namely, the transmittance of the obtained decorated film was low, the crosslinking density inside the cured product was low, generation of out gas was significant, and the water resistance was low. Furthermore, when a urethane acrylamide of an adduct type is used for preparing a composition, the transmittance and light resistance of the composition were low, and the crystallinity inside the cured product was high. Accordingly, the degree of freedom of the vinyl group is suppressed, and thus it was difficult to have complete loss of the vinyl group.

When the urethane modified (meth)acrylamide of the present invention is used, a case of having somewhat low light resistance was confirmed, but the curing property of the sealing agent was high and the crosslinking density inside the cured product was high. For such reasons, the water resistance was high and generation of out gas can be sufficiently suppressed. The heat cycle resistance was high, too.

Evaluation Example H-1

3 parts by weight of the urethane modified (meth)acrylamide UY-1 synthesized in Synthesis Example 1, 5 parts by weight of the urethane modified (meth)acrylamide UY-2 synthesized in Synthesis Example 2, 28 parts by weight of the urethane polymer UP-1 synthesized in Synthesis Example 8, 50 parts by weight of the reactive urethane polymer UP-3 synthesized in Synthesis Example 10, 10 parts by weight of DPHA, 4 parts by weight of IBOA, and 50 parts by weight of MEK were admixed with one another. Then, 3 parts by weight of Irgacure 184 as a photopolymerization initiator was added thereto, and the resulting product was homogeneously mixed, and thus a resin composition for decorative film was produced.

Method for Producing Photocuring Type Decorative Film

The obtained resin composition for decorative film was applied on a PET film ("Softshine TA009" manufactured by Toyobo Co., Ltd.) having a thickness of 125 μm using a bar coater (RDS 30) such that the thickness of the dried film became 20 μm. Thereafter, according to drying for 1 minute at 100° C., a molded film before ultraviolet ray curing was prepared. After that, according to ultraviolet ray irradiation (ultraviolet illumination intensity: 700 mW/cm$^2$, cumulative amount of light: 2,000 mJ/cm$^2$), a decorative film was produced. Each of the molded film before ultraviolet ray curing and the decorative film was evaluated according to the following methods. The results are shown in Table 9.

(48) Transparency

By using the obtained molded film before ultraviolet ray curing, the transmittance of the cured film was measured using a haze meter (NDH-2000 manufactured by Nippon Denshoku Industries Co., Ltd.). The transparency was evaluated based on the four levels that are described below.

⊙: transmittance is 90% or greater
◯: transmittance is 85% or greater but less than 90%
Δ: transmittance is 50% or greater but less than 85%
x: transmittance is less than 50%

(49) Blocking Resistance

On top of the molded film before ultraviolet ray curing obtained above, a non-treated PET ("Cosmoshine A4100" manufactured by Toyobo Co., Ltd., one side was not anchor-coat-treated, having a thickness of 100 μm) was overlaid. By reciprocally moving two times a pressure roller of a load of 2 kg on top of the non-treated PET, pressure-adhesion was performed, and the resulting product was allowed to stand for 30 minutes in an environment with temperature of 23° C. and humidity of 50%. Thereafter, the non-treated PET was peeled off. Blocking resistance was then evaluated according to a naked eye observation.

⊙: There is no adhesion to the non-treated PET, and no change in the outer appearance of the molded film
◯: There is no adhesion to the non-treated PET, but marks remain on part of the surface of the molded film
Δ: There is no migration to the non-treated PET, but marks remain on the entire surface of the molded film
x: There is migration to the non-treated PET, and peeling or floating is shown on the surface of the molded film

(50) Elongation at Break

Measurement was performed, at a temperature of 130° C. and speed of 10 mm/min, by using the molded film before ultraviolet ray curing obtained in the above.

Device for measurement; Tensilon Universal Tester RTA-100 (manufactured by Orientec Co., Ltd.)

Elongation at break (%)=Sheet length at break/Sheet length before test×100

⊚: elongation at break is 100% or higher
○: elongation at break is 50% or higher but lower than 100%
Δ: elongation at break is 10% or higher but lower than 50%
x: elongation at break is lower than 10%

(51) Molding Processability Test

The obtained molded film before ultraviolet ray curing was subjected to molding processing at heating temperature of 130° C. by using a pressure molding machine SDF400 (manufactured by Sodick Co., Ltd.). After cooling to 25° C., the state of the decorative layer of the molded article was determined with a naked eye.

⊚: absolutely no fissure is observed, and the surface has high transparency.
○: although no fissure is observed, there is unevenness in thickness of a decorative layer, thus showing partial decrease in transparency.
Δ: fissure or slight cracks are observed, and unevenness in thickness of a decorative layer or a decrease in transparency is observed.
x: many cracks are observed, and unevenness in thickness of a decorative layer or a decrease in transparency is significant.

(52) Curing Property

The coated resin composition for decorative film was dried for 1 minute at 100° C. After that, it was irradiated with ultraviolet rays of ultraviolet illumination intensity of 700 mW/cm$^2$ under an environment with room temperature of 23° C., and the cumulative amount of light required to have complete curing of the resin composition was measured. The complete curing means a state in which when the surface of the cured film is rubbed with silicone rubber, there is no trace.

⊚: completely cured at a cumulative amount of light of 1,000 mJ/cm$^2$.
○: completely cured at a cumulative amount of light of 1,000 mJ/cm$^2$ to 2,000 mJ/cm$^2$.
Δ: completely cured at a cumulative amount of light of 2,000 mJ/cm$^2$ to 5,000 mJ/cm$^2$.
x: a cumulative amount of light of 5,000 mJ/cm$^2$ or greater is required to have complete curing.

(52) Adhesion Property

According to JIS K 5600, one hundred of squares of 1 mm×1 mm were created by using the obtained decorative film. Then, a cellophane tape was attached thereto, and evaluation was performed by counting the number of squares in which the coating film remained on the substrate side when the tape was peeled all at once.

(53) Pencil Hardness

The evaluation was carried out based on JIS K 5600 by using the obtained decorative film. Namely, when the decorative film was scratched by a pencil for 10 mm or so at an angle of 45°, the hardness of the hardest pencil not yielding any scratches on a surface of the decorative film was determined as pencil hardness, and the evaluation was made accordingly.

⊚: pencil hardness is 2H or higher
○: pencil hardness is HB to H
Δ: pencil hardness is 3B to B
x: pencil hardness is 4B or lower

(54) Scratch Resistance

Steel wool of #0000 was reciprocally moved on the decorative film ten times while a load of 200 g/cm$^2$ was applied, and the presence of an occurrence of scratches was evaluated with a naked eye.

⊚: peeling of a film or occurrence of scratches is hardly observed.
○: fine scratches are slightly observed on a part of a film.
Δ: streaky scratches are observed on the entire film surface.
x: peeling of a film occurs.

(55) Bending Resistance

The decorative film obtained in the above was bent such that the coating surface faces the outside. After applying a pressurizing stone of 1 kg thereto, it was allowed to stand for 10 minutes. Then, the presence or absence of cracks on a surface of the decorative film was observed with a naked eye.

⊚: absolutely no cracks were observed.
○: bent part was partially whitened.
Δ: cracks were observed from part of the bent part.
x: cracks were observed from the bent part.

Evaluation Examples H-2 to 7 and Comparative Evaluation Examples H-8 to 11

A resin composition for decorative film was prepared in the same manner as Evaluation Example H-1 except that the composition described in Table 9 is used instead. A decorative film was produced according to the methods described above. The evaluation was made based on the methods described above. The results are shown in Table 9.

As shown in the results of the Evaluation examples and the Comparative evaluation examples, the following tendency was shown when the urethane modified (meth)acrylamide which has a molecular weight and acryl equivalents that are outside the specific range, or the urethane modified (meth)acrylate which has a molecular weight and acryl equivalents that are within the specific range is blended. Namely, the molded film before ultraviolet ray curing was soft, and tack was also exhibited. Due to such reasons, the blocking resistance was poor, and it is difficult to obtain elongation at high temperature conditions. Furthermore, among the obtained decorative films, a decorative film with high bending resistance was also confirmed. However, as the cured product is soft, the scratch resistance was low.

When the urethane modified (meth)acrylamide of the present invention is used, an aggregation between the amide group and urethane bond forms a quasi hard segment. Accordingly, high blocking resistance and molding processability were exhibited. As such, a molded film before ultraviolet curing having no cracks was obtained. Furthermore, at high temperatures like temperature equal to or higher than Tg of the urethane polymer and Tg of the urethane modified (meth)acrylamide, the quasi hard segment is temporarily dispersed. Accordingly, high elongation at break is exhibited. At a high room temperature like a temperature equal to or lower than Tg, it was possible to obtain a decorative film having pencil hardness and scratch resistance.

TABLE 1

| | Solvent Monomer | Evaluation Example | | | | | | | Comparative Evaluation Example |
|---|---|---|---|---|---|---|---|---|---|
| | | UY-1 | UY-2 | UY-3 | UY-4 | UY-5 | UY-6 | UY-7 | UA-5 |
| Compatibility | IPA | ○ | ○ | ○ | ○ | ○ | ○ | ○ | ○ |
| | MEK | ○ | ○ | ○ | ○ | ○ | ○ | ○ | ○ |
| | THF | ○ | ○ | ○ | ○ | ○ | ○ | ○ | ○ |
| | Ethyl acetate | ○ | ○ | ○ | ○ | Δ | ○ | ○ | X |
| | Toluene | ○ | ○ | ○ | ○ | ○ | ○ | ○ | X |
| | ACMO | ○ | Δ | ○ | Δ | X | Δ | ○ | ○ |
| | HDDA | ○ | X | Δ | Δ | X | Δ | ○ | X |
| | BA | ○ | Δ | ○ | ○ | X | ○ | ○ | X |
| | IBOA | ○ | Δ | Δ | Δ | ○ | ○ | ○ | X |
| | 2EHA | ○ | ○ | ○ | ○ | ○ | ○ | ○ | X |
| | THEA | ○ | ○ | ○ | ○ | Δ | ○ | ○ | X |

TABLE 2

| | | Evaluation Example | | | | | | | Comparative Evaluation Example | | | |
|---|---|---|---|---|---|---|---|---|---|---|---|---|
| | | A-1 | A-2 | A-3 | A-4 | A-5 | A-6 | A-7 | A-8 | A-9 | A-10 | A-11 |
| Urethane oligomer | UY-1 | 100 | | | | | | | | | | |
| | UY-2 | | 100 | | | | | | | | | |
| | UY-3 | | | 100 | | | | | | | | |
| | UY-4 | | | | 100 | | | | | | | |
| | UY-5 | | | | | 100 | | | | | | |
| | UY-6 | | | | | | 100 | | | | | |
| | UY-7 | | | | | | | 100 | | | | |
| | UA-1 | | | | | | | | 100 | | | |
| | UA-2 | | | | | | | | | 100 | | |
| | UA-3 | | | | | | | | | | 100 | |
| | UA-4 | | | | | | | | | | | 100 |
| Photopolymerization initiator | Irgacure 1173 | 3 | 3 | 3 | 3 | 3 | 3 | 3 | 3 | 3 | 3 | 3 |
| Characteristics of cured product | Curing property | ⊙ | ⊙ | ⊙ | ⊙ | ⊙ | ⊙ | ⊙ | ○ | ⊙ | X | X |
| | Tack resistance | ⊙ | ⊙ | ⊙ | ⊙ | ⊙ | ⊙ | ⊙ | ⊙ | Δ | Δ | ⊙ |
| | Curl resistance | ⊙ | ⊙ | ⊙ | ⊙ | ⊙ | ⊙ | ⊙ | Δ | ○ | Δ | X |
| | Transparency | ⊙ | ⊙ | ⊙ | ⊙ | ⊙ | ⊙ | ⊙ | Δ | ○ | ⊙ | Δ |
| | Water absorption rate [%] | 0.8 | 0.5 | 1.8 | 0.4 | 0.2 | 0.6 | 1.5 | 1.2 | 2.8 | 2.5 | 3.2 |
| | Adhesion property PET (easy adhesion) | 100/100 | 100/100 | 100/100 | 100/100 | 100/100 | 100/100 | 100/100 | 100/100 | 100/100 | 100/100 | 100/100 |
| | PET (non-treated) | 100/100 | 100/100 | 80/100 | 100/100 | 100/100 | 100/100 | 80/100 | 0/100 | 20/100 | 0/100 | 0/100 |
| | PC | 100/100 | 100/100 | 100/100 | 100/100 | 70/100 | 100/100 | 100/100 | 100/100 | 0/100 | 0/100 | 0/100 |
| | PMMA | 80/100 | 80/100 | 100/100 | 70/100 | 70/100 | 90/100 | 100/100 | 0/100 | 80/100 | 0/100 | 0/100 |
| | ABS | 100/100 | 100/100 | 100/100 | 100/100 | 70/100 | 80/100 | 100/100 | 100/100 | 0/100 | 0/100 | 0/100 |

TABLE 3

| | | Evaluation Example | | | | | | | Comparative Evaluation Example | | | |
|---|---|---|---|---|---|---|---|---|---|---|---|---|
| | | B-1 | B-2 | B-3 | B-4 | B-5 | B-6 | B-7 | B-8 | B-9 | B-10 | B-11 |
| Urethane modified acrylamide | UY-1 | 8 | | | | | | | | | | |
| | UY-2 | | 12 | | | | | | | | | |
| | UY-3 | | | 20 | | | | | | | | |
| | UY-4 | | | | 13 | | | | | | | |
| | UY-5 | | | | | 8 | | | | | | |
| | UY-6 | | | | | | 10 | | | | | |
| | UY-7 | | | | | | | 5 | | | | |
| | UA-1 | | | | | | | | 12 | | | |
| | UA-2 | | | | | | | | | 10 | | |
| | UA-3 | | | | | | | | | | 7 | |
| | UA-4 | | | | | | | | | | | 5 |

TABLE 3-continued

|  |  | Evaluation Example |  |  |  |  |  |  | Comparative Evaluation Example |  |  |  |
|---|---|---|---|---|---|---|---|---|---|---|---|---|
|  |  | B-1 | B-2 | B-3 | B-4 | B-5 | B-6 | B-7 | B-8 | B-9 | B-10 | B-11 |
| Poly-functional compound | UP-3 |  | 28 |  | 25 |  |  |  |  | 12 |  | 20 |
|  | Hitaroid 7851 |  |  |  |  |  | 5 |  |  | 10 |  |  |
|  | Hitaroid 7975 | 5 |  | 4 |  |  |  |  |  |  |  |  |
|  | UP-4 | 25 |  | 20 |  | 32 | 25 | 20 | 28 |  | 28 |  |
| Other monomers | "HEAA" | 10 | 25 | 20 | 15 | 13 | 12 | 10 | 15 | 13 | 25 | 15 |
|  | "DEAA" | 30 |  |  | 17 | 22 |  | 23 | 10 | 24 | 15 | 8 |
|  | 2EHA |  | 22 | 29 |  | 17 | 25 | 22 | 14 |  | 22 | 22 |
|  | CHA | 4 |  | 9 |  | 8 |  | 10 |  | 25 |  | 23 |
|  | EEA | 15 | 8 |  | 15 |  | 20 |  | 16 | 6 |  |  |
| Ionic vinyl monomer | DMAEA-TFSIQ |  | 5 | 2 |  |  |  | 7 | 5 |  |  |  |
|  | DMAPAA-TFSIQ | 3 |  | 7 |  | 3 |  |  |  |  | 3 | 7 |
| Photopoly-merization initiator | Irgacure 184 | 1 | 1 | 1 | 1 | 1 | 1 | 1 | 1 | 1 | 1 | 1 |
| Charac-teristics of cohesive sheet | Transparency | 100 | 100 | 100 | 100 | 100 | 100 | 100 | 88 | 100 | 100 | 95 |
|  | Surface resistance value [Ω/□] | 4.5 * $10^{11}$ | 7.8 * $10^{8}$ | 6.5 * $10^{10}$ | 8.2 * $10^{7}$ | 2.0 * $10^{12}$ | 3.6 * $10^{9}$ | 7.5 * $10^{7}$ | 6.8 * $10^{9}$ | 7.3 * $10^{13}$ | 5.2 * $10^{10}$ | 2.2 * $10^{9}$ |
|  | Cohesive force PET | ⊙ | ⊙ | ⊙ | ⊙ | ⊙ | ⊙ | ⊙ | ○ | ○ | △ | ○ |
|  | Glass | ⊙ | ○ | ⊙ | ○ | ⊙ | ○ | ⊙ | X | ○ | △ | △ |
|  | Contam-ination resistance PET | ○ | ⊙ | ○ | ⊙ | ○ | ⊙ | ○ | ○ | △ | ○ | X |
|  | Glass | ○ | ⊙ | ○ | ⊙ | ○ | ⊙ | ○ | △ | △ | ○ | X |
|  | Yellowing resistance | ⊙ | ⊙ | ⊙ | ○ | ⊙ | ⊙ | ⊙ | △ | X | ⊙ | ○ |
|  | Moisture and heat resistance | ○ | ⊙ | ⊙ | ○ | ⊙ | ○ | ⊙ | ○ | X | △ | X |
|  | Step followability | ⊙ | ⊙ | ⊙ | ○ | ⊙ | ○ | ⊙ | △ | ○ | ⊙ | X |
|  | Punching processability | ○ | ⊙ | ⊙ | ⊙ | ○ | ⊙ | ○ | ○ | X | △ | ○ |

TABLE 4

|  |  | Evaluation Example |  |  |  |  |  |  | Comparative Evaluation Example |  |  |  |
|---|---|---|---|---|---|---|---|---|---|---|---|---|
|  |  | C-1 | C-2 | C-3 | C-4 | C-5 | C-6 | C-7 | C-8 | C-9 | C-10 | C-11 |
| Urethane modified acrylamide | UY-1 | 22 |  |  |  |  |  |  |  |  |  |  |
|  | UY-2 |  | 12 |  |  |  |  |  |  |  |  |  |
|  | UY-3 |  |  | 8 |  |  |  |  |  |  |  |  |
|  | UY-4 |  |  |  | 24 |  |  |  |  |  |  |  |
|  | UY-5 |  |  |  |  | 22 |  |  |  |  |  |  |
|  | UY-6 |  |  |  |  |  | 27 |  |  |  |  |  |
|  | UY-7 |  |  |  |  |  |  | 30 |  |  |  |  |
|  | UA-1 |  |  |  |  |  |  |  | 13 |  |  |  |
|  | UA-2 |  |  |  |  |  |  |  |  | 25 |  |  |
|  | UA-3 |  |  |  |  |  |  |  |  |  | 20 |  |
|  | UA-4 |  |  |  |  |  |  |  |  |  |  | 28 |
| Polyfunctional compound | UP-3 | 11 | 18 | 20 | 12 | 14 | 18 | 15 | 17 | 22 | 23 | 10 |
|  | Hitaroid 7851 | 4 |  | 10 |  |  |  | 5 |  |  |  | 5 |
|  | Hitaroid 7975 |  |  |  |  | 3 | 2 |  |  |  |  |  |
| Other monomers | "ACMO" | 18 | 14 | 12 |  | 21 | 10 | 13 | 25 |  |  | 17 |
|  | "HEAA" | 9 | 13 |  | 13 | 20 | 10 | 20 | 15 | 10 |  | 20 |
|  | "DMAA" | 14 |  | 22 |  |  |  |  |  |  | 10 |  |
|  | "DMAPAA" |  | 24 |  | 14 |  | 25 | 7 |  | 6 | 11 | 10 |
|  | HEA |  |  | 12 |  | 15 |  |  | 18 | 15 | 18 |  |
|  | THFA | 10 | 19 | 16 | 12 | 5 |  |  | 12 | 10 |  | 10 |
|  | IBOA | 12 |  |  | 25 |  | 8 | 10 |  | 12 | 18 |  |
| Photopolymerization initiator | Irgacure 1173 | 3 | 3 | 3 | 3 | 3 | 3 | 3 | 3 | 3 | 3 | 3 |
| Characteristics of polarizing plate | Observation of surface shape | ⊙ | ⊙ | ⊙ | ⊙ | ⊙ | ⊙ | ⊙ | △ | ⊙ | ○ | △ |
|  | Peeling strength | ⊙ | ⊙ | ○ | ⊙ | ⊙ | ○ | ⊙ | ○ | △ | △ | ○ |
|  | Water resistance | ⊙ | ⊙ | ⊙ | ⊙ | ⊙ | ⊙ | ⊙ | ⊙ | X | △ | △ |
|  | Durability | ⊙ | ⊙ | ⊙ | ⊙ | ⊙ | ⊙ | ⊙ | △ | △ | △ | X |

TABLE 5

|  |  | Evaluation Example |  |  |  |  |  |  | Comparative Evaluation Example |  |  |  |
|---|---|---|---|---|---|---|---|---|---|---|---|---|
|  |  | D-1 | D-2 | D-3 | D-4 | D-5 | D-6 | D-7 | D-8 | D-9 | D-10 | D-11 |
| Urethane modified acrylamide | UY-1 | 48 | | | | | | | | | | |
|  | UY-2 | | 23 | | | | | | | | | |
|  | UY-3 | | | 45 | | | | | | | | |
|  | UY-4 | | | | 20 | | | | | | | |
|  | UY-5 | | | | | 32 | | | | | | |
|  | UY-6 | | | | | | 15 | | | | | |
|  | UY-7 | | | | | | | 38 | | | | |
|  | UA-1 | | | | | | | | 40 | | | |
|  | UA-2 | | | | | | | | | 28 | | |
|  | UA-3 | | | | | | | | | | 45 | |
|  | UA-4 | | | | | | | | | | | 12 |
| Polyfunctional compound | UP-1 | | | 10 | | 12 | 13 | | 15 | | | |
|  | Hitaroid 7851 | | | 5 | | 3 | | | | | 5 | |
|  | Hitaroid 7975 | | | 5 | | | 2 | | 5 | | | |
|  | UP-3 | | 5 | | 10 | | 5 | | 8 | 25 | | 20 |
|  | HDDA | 15 | 16 | 5 | 18 | 15 | 12 | 15 | | 15 | 17 | 15 |
|  | TPGDA | 24 | 22 | | 22 | | 18 | 25 | 15 | | | |
| Other monomers | "DEAA" | 8 | | 15 | | 23 | 13 | 10 | | 12 | 20 | 17 |
|  | THEA | | 22 | 5 | 10 | | | | 7 | 10 | 8 | 10 |
|  | VEEA | | 12 | 10 | | 15 | | 12 | | | | |
|  | IBOA | 5 | | | 20 | | 22 | | 10 | 10 | 5 | 26 |
| Pigment | | 3 | 3 | 3 | 3 | 3 | 3 | 3 | 3 | 3 | 3 | 3 |
| Pigment dispersing agent | | 3 | 3 | 3 | 3 | 3 | 3 | 3 | 3 | 3 | 3 | 3 |
| Photopolymerization initiator | Irgacure 819 | 2 | 2 | 2 | 2 | 2 | 2 | 2 | 2 | 2 | 2 | 2 |
|  | Irgacure 127 | 3 | 3 | 3 | 3 | 3 | 3 | 3 | 3 | 3 | 3 | 3 |
| Characteristics of printed matter | Viscosity [mPa · S] | 12 | 17 | 8 | 15 | 15 | 12 | 5 | 32 | 22 | 3 | 25 |
|  | Compatibility | ⊙ | ⊙ | ⊙ | ⊙ | ○ | ⊙ | ⊙ | Δ | ○ | ○ | Δ |
|  | Curing property | ⊙ | ⊙ | ⊙ | ⊙ | ⊙ | ⊙ | ⊙ | ○ | ○ | X | Δ |
|  | Surface dryness | ⊙ | ⊙ | ⊙ | ⊙ | ⊙ | ⊙ | ⊙ | ○ | Δ | X | Δ |
|  | Discharge stability | ⊙ | ○ | ⊙ | ○ | ⊙ | ⊙ | ⊙ | X | Δ | ○ | Δ |
|  | Sharpness | ⊙ | ⊙ | ⊙ | ⊙ | ⊙ | ⊙ | ⊙ | Δ | Δ | X | X |
|  | Water resistance | ⊙ | ⊙ | ○ | ○ | ⊙ | ⊙ | ○ | Δ | X | Δ | Δ |

TABLE 6

|  |  |  | Evaluation Example |  |  |  |  |  |  | Comparative Evaluation Example |  |  |  |
|---|---|---|---|---|---|---|---|---|---|---|---|---|---|
|  |  |  | E-1 | E-2 | E-3 | E-4 | E-5 | E-6 | E-7 | E-8 | E-9 | E-10 | E-11 |
| Urethane modified acrylamide | UY-1 | | 15 | | | | 8 | | | | | | |
|  | UY-2 | | | 25 | 3 | | | | | | | | |
|  | UY-3 | | | | 15 | 23 | | | | | | | |
|  | UY-4 | | | | | 10 | | | | | | | |
|  | UY-5 | | | | | | 5 | | | | | | |
|  | UY-6 | | | | | | | 10 | | | | | |
|  | UY-7 | | | | | | | 5 | 12 | | | | |
|  | UA-1 | | | | | | | | | 22 | | | |
|  | UA-2 | | | | | | | | | | 8 | | |
|  | UA-3 | | | | | | | | | | | 13 | |
|  | UA-4 | | | | | | | | | | | | 5 |
| Polyfunctional compound | UP-1 | | 10 | | 10 | | 55 | 15 | 10 | | 10 | 20 | 5 |
|  | Hitaroid 7851 | | | 10 | 20 | | 10 | | | | | | |
|  | Hitaroid 7975 | | 20 | 10 | | 10 | | 10 | | | 10 | | |
|  | UP-3 | | 20 | 28 | 30 | 27 | | 30 | 45 | 40 | 22 | 30 | 50 |
|  | PETA | | 25 | 10 | | | | | 12 | | 12 | | 15 |
|  | DPHA | | | | 12 | 10 | 12 | | 8 | 25 | 13 | 15 | |
| Other monomers | "ACMO" | | 5 | | | 5 | | 13 | 13 | | 12 | 12 | |
|  | "DMAA" | | | | 10 | | | 8 | | | 15 | | |
|  | THFA | | | | | 5 | 5 | | 12 | | | 10 | 13 |
|  | IBOA | | 10 | 12 | | 15 | | 10 | | | 10 | | |
| Solvent | MEK | | | 20 | | 20 | 20 | 20 | | | | | |
| Photopolymerization initiator | Irgacure 1173 | | 3 | 3 | 3 | 3 | 3 | 3 | 3 | 3 | 3 | 3 | 3 |
| Characteristics of coating film | Compatibility | | ⊙ | ⊙ | ⊙ | ⊙ | ⊙ | ○ | ⊙ | ○ | ⊙ | ⊙ | ⊙ |
|  | Wettability | PET (easy adhesion) | ⊙ | ⊙ | ⊙ | ⊙ | ⊙ | ⊙ | ⊙ | ⊙ | ○ | ○ | ○ |
|  |  | PET (non-treated) | ⊙ | ⊙ | ○ | ⊙ | ⊙ | ⊙ | ○ | Δ | X | Δ | X |
|  |  | PC | ⊙ | ⊙ | ⊙ | ⊙ | ⊙ | ○ | ⊙ | ⊙ | ○ | Δ | Δ |
|  |  | PMMA | ⊙ | ⊙ | ⊙ | ⊙ | ⊙ | ⊙ | ○ | X | ○ | Δ | X |

TABLE 6-continued

|  |  | Evaluation Example |  |  |  |  |  |  | Comparative Evaluation Example |  |  |  |
|---|---|---|---|---|---|---|---|---|---|---|---|---|
|  |  | E-1 | E-2 | E-3 | E-4 | E-5 | E-6 | E-7 | E-8 | E-9 | E-10 | E-11 |
|  | Curing property | ⊙ | ⊙ | ⊙ | ⊙ | ⊙ | ⊙ | ⊙ | ○ | ○ | Δ | X |
|  | Tack resistance | ○ | ⊙ | ○ | ⊙ | ⊙ | ⊙ | ○ | ⊙ | Δ | Δ | X |
|  | Shrinkage resistance | ⊙ | ○ | ⊙ | ⊙ | ⊙ | ⊙ | ⊙ | ⊙ | ⊙ | ○ | Δ |
|  | Scratch resistance | ○ | ⊙ | ○ | ○ | ⊙ | ○ | ⊙ | Δ | Δ | X | X |
|  | Self restoring property | ⊙ | ⊙ | ○ | ○ | ⊙ | ○ | ○ | X | X | X | X |
| Adhesion property | PET (easy adhesion) | 100/100 | 100/100 | 100/100 | 100/100 | 100/100 | 100/100 | 100/100 | 100/100 | 100/100 | 90/100 | 50/100 |
|  | PET (non-treated) | 100/100 | 100/100 | 90/100 | 90/100 | 90/100 | 70/100 | 100/100 | 70/100 | 60/100 | 0/100 | 0/100 |
|  | PC | 100/100 | 100/100 | 100/100 | 100/100 | 70/100 | 90/100 | 90/100 | 100/100 | 40/100 | 50/100 | 30/100 |
|  | Acryl plate | 100/100 | 100/100 | 100/100 | 100/100 | 70/100 | 100/100 | 80/100 | 60/100 | 0/100 | 20/100 | 0/100 |
| Moisture resistance |  | ⊙ | ⊙ | ○ | ⊙ | ⊙ | ⊙ | ○ | ⊙ | Δ | ○ | X |

TABLE 7

|  |  | Evaluation Example |  |  |  |  |  |  | Comparative Evaluation Example |  |  |  |
|---|---|---|---|---|---|---|---|---|---|---|---|---|
|  |  | F-1 | F-2 | F-3 | F-4 | F-5 | F-6 | F-7 | F-8 | F-9 | F-10 | F-11 |
| Urethane modified acrylamide | UY-1 | 32 |  |  |  |  |  |  |  |  |  |  |
|  | UY-2 |  | 18 |  |  | 5 |  |  |  |  |  |  |
|  | UY-3 |  |  | 20 |  |  |  |  |  |  |  |  |
|  | UY-4 |  |  |  | 12 |  |  |  |  |  |  |  |
|  | UY-5 |  |  |  |  | 20 |  |  |  | 10 |  |  |
|  | UY-6 | 5 |  | 18 | 10 | 20 | 22 | 15 |  |  | 5 |  |
|  | UY-7 |  |  |  |  |  | 15 | 10 |  |  |  |  |
|  | UA-1 |  |  |  |  |  |  | 25 |  |  |  |  |
|  | UA-2 |  |  |  |  |  |  |  |  | 15 |  |  |
|  | UA-3 |  |  |  |  |  |  |  |  |  | 25 |  |
|  | UA-4 |  |  |  |  |  |  |  |  |  |  | 22 |
| Polyfunctional compound | UP-2 | 20 | 25 | 25 | 28 | 25 | 15 | 25 | 20 | 20 | 25 | 18 |
|  | Hitaroid 7851 |  |  |  | 2 |  | 5 |  |  | 2 |  |  |
|  | Hitaroid 7975 | 2 |  |  |  |  | 5 |  |  |  |  |  |
| Other monomers | "HEAA" |  | 22 | 15 | 25 | 12 |  | 15 | 10 | 15 | 10 | 15 |
|  | "ACMO" | 5 |  |  | 18 |  | 12 |  | 8 | 22 | 10 | 5 |
|  | IBMA | 21 | 25 | 12 | 15 | 21 | 23 | 23 | 12 | 16 | 15 | 22 |
|  | CHMA | 15 | 10 | 10 |  | 12 | 15 |  |  |  | 10 | 18 |
| Photopolymerization initiator | Irgacure 184 | 3 | 3 | 3 | 3 | 3 | 3 | 3 | 3 | 3 | 3 | 3 |
| Characteristics of finger nail decorating agent | Curing property | ⊙ | ⊙ | ⊙ | ⊙ | ⊙ | ⊙ | ⊙ | ⊙ | ⊙ | Δ | Δ |
|  | Smoothness | ⊙ | ○ | ⊙ | ○ | ⊙ | ⊙ | ○ | Δ | Δ | ○ | X |
|  | Glossiness | ⊙ | ○ | ○ | ○ | ⊙ | ⊙ | ○ | ○ | X | ○ | X |
|  | Adhesion property | ⊙ | ⊙ | ○ | ⊙ | ⊙ | ⊙ | ○ | ○ | X | Δ | X |
|  | Removability | ⊙ | ⊙ | ○ | ⊙ | ○ | ○ | ⊙ | Δ | ○ | X | ○ |

TABLE 8

|  |  | Evaluation Example |  |  |  |  |  |  | Comparative Evaluation Example |  |  |  |  |
|---|---|---|---|---|---|---|---|---|---|---|---|---|---|
|  |  | G-1 | G-2 | G-3 | G-4 | G-5 | G-6 | G-7 | G-8 | G-9 | G-10 | G-11 | G-12 |
| Urethane modified acrylamide | UY-1 | 24 |  |  |  |  |  |  |  |  |  |  |  |
|  | UY-2 | 12 | 20 | 10 |  |  |  |  |  |  |  |  |  |
|  | UY-3 |  |  | 25 | 15 |  |  |  |  |  |  |  |  |
|  | UY-4 |  |  |  | 10 |  |  |  |  |  |  |  |  |
|  | UY-5 |  |  |  |  | 12 |  |  |  |  |  |  |  |
|  | UY-6 |  |  |  |  |  | 7 | 15 |  | 10 |  |  |  |
|  | UY-7 |  |  |  |  |  |  | 10 | 30 |  |  |  |  |
|  | UA-1 |  |  |  |  |  |  |  |  | 15 |  |  |  |
|  | UA-2 |  |  |  |  |  |  |  |  |  | 15 |  | 12 |
|  | UA-3 |  |  |  |  |  |  |  |  |  |  | 20 |  |

TABLE 8-continued

|  |  | Evaluation Example | | | | | | | Comparative Evaluation Example | | | | |
| --- | --- | --- | --- | --- | --- | --- | --- | --- | --- | --- | --- | --- | --- |
|  |  | G-1 | G-2 | G-3 | G-4 | G-5 | G-6 | G-7 | G-8 | G-9 | G-10 | G-11 | G-12 |
|  | UA-4 |  |  |  |  |  |  |  |  |  |  | 10 |  |
|  | UA-5 |  |  |  |  |  |  |  |  |  |  |  | 25 |
| Polyfunctional compound | UP-1 | 20 |  | 15 |  | 25 | 12 | 15 | 20 |  | 15 |  | 10 |
|  | Hitaroid 7851 | 5 |  | 15 |  |  | 3 | 15 |  |  |  |  |  |
|  | Hitaroid 7975 |  |  |  | 3 |  |  |  |  | 10 |  | 5 |  |
|  | UP-2 | 5 | 25 |  | 30 | 5 | 10 |  | 15 | 12 | 20 | 30 | 15 |
| Monomer | "ACMO" | 10 |  |  | 5 | 5 | 15 | 5 |  | 12 | 15 |  | 10 |
|  | "HEAA" |  | 10 |  | 15 |  | 10 |  |  |  |  | 10 |  |
|  | "DEAA" | 4 | 8 | 7 |  | 8 |  | 10 | 15 | 20 | 10 |  |  |
|  | 4HBA | 10 | 15 | 10 |  | 12 | 10 |  |  | 16 |  | 13 | 10 |
|  | A-LEN-10 | 10 | 12 | 5 | 13 | 13 |  | 5 | 10 |  | 5 | 8 | 13 |
|  | IBOA |  | 10 | 13 | 12 | 10 | 15 | 20 | 15 | 15 | 15 | 12 | 17 |
| Photopolymerization initiator | Irgacure 184 | 2 | 2 | 2 | 2 | 2 | 2 | 2 | 2 | 2 | 2 | 2 | 2 |
|  | Irgacure TPO | 2 | 2 | 2 | 2 | 2 | 2 | 2 | 2 | 2 | 2 | 2 | 2 |
| Characteristics of sealing agent | Transmittance (%) | ⊙ | ⊙ | ⊙ | ⊙ | ○ | ⊙ | ⊙ | ○ | Δ | ○ | ○ | X |
|  | Light resistance | ○ | ⊙ | ⊙ | ○ | ⊙ | ⊙ | ○ | ○ | Δ | Δ | ○ | X |
|  | Water resistance | ⊙ | ⊙ | ○ | ○ | ⊙ | ○ | ○ | ○ | X | Δ | X | X |
|  | Evaluation of out gas generation | ○ | ○ | ⊙ | ○ | ○ | ○ | ○ | X | Δ | Δ | Δ | X |
|  | Heat cycle resistance | ⊙ | ⊙ | ○ | ○ | ⊙ | ○ | ⊙ | Δ | Δ | X | X | X |

TABLE 9

|  |  | Evaluation Example | | | | | | | Comparative Evaluation Example | | | |
| --- | --- | --- | --- | --- | --- | --- | --- | --- | --- | --- | --- | --- |
|  |  | H-1 | H-2 | H-3 | H-4 | H-5 | H-6 | H-7 | H-8 | H-9 | H-10 | H-11 |
| Urethane modified acrylamide | UY-1 | 3 |  |  | 2 |  |  |  |  |  |  |  |
|  | UY-2 | 5 | 13 |  |  |  |  |  |  |  |  |  |
|  | UY-3 |  |  | 18 |  | 8 |  |  |  |  |  |  |
|  | UY-4 |  |  |  | 8 |  |  |  |  |  |  |  |
|  | UY-5 |  |  |  |  | 8 |  |  |  |  |  |  |
|  | UY-6 |  |  |  |  |  | 10 |  |  |  |  |  |
|  | UY-7 |  |  |  |  |  |  | 5 |  |  |  |  |
|  | UA-1 |  |  |  |  |  |  |  | 2 |  |  |  |
|  | UA-2 |  |  |  |  |  |  |  |  | 10 |  |  |
|  | UA-3 |  |  |  |  |  |  |  | 5 |  | 8 |  |
|  | UA-4 |  |  |  |  |  |  |  |  |  |  | 12 |
| Polyfunctional compound | UP-1 | 28 | 30 | 30 | 20 | 45 | 22 | 30 | 30 | 25 | 23 | 50 |
|  | Hitaroid 7851 |  | 10 |  |  |  |  | 10 |  |  | 5 |  |
|  | Hitaroid 7975 | 15 |  |  |  |  | 20 |  | 20 |  |  |  |
|  | UP-3 | 35 | 25 | 40 | 40 | 20 | 30 | 40 | 20 | 40 | 35 | 20 |
|  | HDDA |  | 5 |  | 5 | 5 |  | 5 | 5 |  |  |  |
|  | DPHA | 10 | 10 | 12 | 20 | 10 | 18 | 10 | 23 | 15 | 20 | 12 |
| Other monomers | "ACMO" |  | 7 |  |  | 4 |  |  |  |  | 4 |  |
|  | IBOA | 4 |  |  | 5 |  |  | 5 |  | 5 |  | 6 |
| Solvent | MEK | 50 | 50 | 50 | 50 | 50 | 50 | 50 | 50 | 50 | 50 | 50 |
| Photopolymerization initiator | Irgacure 184 | 3 | 3 | 3 | 3 | 3 | 3 | 3 | 3 | 3 | 3 | 3 |
| Characteristics of decorative film | Transmittance | ⊙ | ⊙ | ⊙ | ⊙ | ○ | ○ | ⊙ | ○ | Δ | ○ | ○ |
|  | Blocking resistance | ⊙ | ⊙ | ⊙ | ⊙ | ○ | ○ | ⊙ | Δ | Δ | Δ | ○ |
|  | Elongation at break | ○ | ⊙ | ⊙ | ⊙ | ○ | ○ | ⊙ | Δ | Δ | X | X |
|  | Molding processability | ⊙ | ⊙ | ⊙ | ⊙ | ○ | ○ | ⊙ | Δ | ○ | Δ | Δ |
|  | Curing property | ⊙ | ⊙ | ⊙ | ⊙ | ⊙ | ⊙ | ⊙ | ⊙ | ○ | X | Δ |
|  | Adhesion property PET (easy adhesion) | 100/100 | 100/100 | 100/100 | 100/100 | 100/100 | 100/100 | 100/100 | 100/100 | 80/100 | 100/100 | 50/100 |
|  | PC | 100/100 | 100/100 | 100/100 | 100/100 | 70/100 | 80/100 | 100/100 | 100/100 | 0/100 | 70/100 | 30/100 |
|  | ABS | 100/100 | 100/100 | 40/100 | 60/100 | 100/100 | 80/100 | 100/100 | 100/100 | 0/100 | 0/100 | 30/100 |
|  | Pencil hardness | ⊙ | ⊙ | ○ | ○ | ○ | ○ | ○ | Δ | ○ | Δ | Δ |
|  | Scratch resistance | ⊙ | ⊙ | ○ | ○ | ○ | ○ | ○ | X | Δ | X | X |
|  | Bending resistance | ⊙ | ○ | ⊙ | ○ | ⊙ | ⊙ | ⊙ | X | ○ | Δ | Δ |

INDUSTRIAL APPLICABILITY

As explained in the above, the urethane modified (meth) acrylamide of the present invention is characterized in that it has a urethane bond and one or more (meth)acrylamide groups in the molecule, and also has a molecular weight and acryl equivalents that are within the specific range. According to ultraviolet ray curing, crosslinking density inside a cured product is increased, and according to an aggregation between the amide group and urethane bonding site, a quasi hard segment can be formed. Due to such reasons, an excellent curing property and tack resistance are obtained.

Other than those, hardness, shrinkage resistance, durability, and the like are exhibited, and also performances like the flexibility, water resistance, and gliding property provided on the main skeleton other than the urethane bond and (meth)acrylamide, namely, main skeleton derived from an alcohol compound, are also exhibited. The urethane modified (meth)acrylamide of the present invention has balance between the hydrophilicity and hydrophobicity and also balance between the hardness and flexibility. By using the urethane modified (meth)acrylamide of the present invention, it was possible to obtain a curable resin composition which has high transparency, adhesion property for various substrates, and scratch resistance. Furthermore, by using the curable resin composition of the present invention either alone, or as a mixture with a monofunctional monomer, a polyfunctional monomer, a general purpose oligomer, a pigment, or the like, if necessary, suitable use for an application including cohesive-adhesives, electronic materials, optic field, semiconductor field, ink, a coating agent, gel nail, a sealing agent, a decorative film, and a resist of photocuring type can be achieved.

The invention claimed is:

1. A urethane modified (meth)acrylamide compound which comprises one or more urethane bonds and one or more (meth)acrylamide groups in the molecule, wherein the urethane modified (meth)acrylamide compound has a number average molecular weight of 250 to 4,500 and an acryl equivalent of 250 to 3,000, which is a molecular weight per one (meth)acrylamide group and is obtained by an addition reaction of an alcohol compound having one or more hydroxyl groups per molecule, wherein the alcohol compound has one or more kinds of a skeleton selected from an ester skeleton, a carbonate skeleton, a silicone skeleton, and an acryl skeleton, an isocyanate compound having two or more isocyanate groups per molecule, and an N-substituted (meth)acrylamide compound containing a hydroxyl group represented by formula [1]

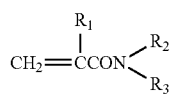

[1]

wherein $R_1$ represents a hydrogen atom or a methyl group, $R_2$ and $R_3$ may be the same or different from each other, $R_2$ and $R_3$ represent a hydrogen atom or a linear or branched alkyl group having 1 to 6 carbon atoms or an aliphatic ring or an aromatic ring having 3 to 6 carbon atoms, which may be substituted with a hydroxyl group, and wherein $R_2$ and $R_3$ may form, together with the nitrogen atom to which they are attached, a saturated or unsaturated 5- to 7-membered ring, in which 5- to 7-membered ring, an oxygen atom or a nitrogen atom other than the aforementioned nitrogen atom may be additionally contained, with the proviso that $R_2$ and $R_3$ are not both a hydrogen atom and $R_2$ and $R_3$ are not both an alkyl group and that $R_2$ and $R_3$ have one or more hydroxyl groups in total.

2. An active energy ray curable resin composition comprising 1 to 100% by weight of the urethane modified (meth)acrylamide compound (A) according to claim 1, 0 to 90% by weight of polyfunctional (meth)acryl compound (B), and 0 to 90% by weight of monofunctional (meth)acryl compound (C).

3. An active energy ray curable cohesive composition comprising the compound according to claim 1.

4. An active energy ray curable adhesive composition comprising the compound according to claim 1.

5. An active energy ray curable inkjet ink composition comprising the compound according to claim 1.

6. An active energy ray curable coating composition comprising the compound according to claim 1.

7. An active energy ray curable coating composition for finger nail decoration comprising the compound according to claim 1.

8. An active energy ray curable sealing agent composition comprising the compound according to claim 1.

9. An active energy ray curable coating composition for decorative film comprising the compound according to claim 1.

10. A urethane modified (meth)acrylamide compound which comprises one or more urethane bonds and one or more (meth)acrylamide groups in the molecule, wherein the urethane modified (meth)acrylamide compound has a number average molecular weight of 250 to less than 3,000 and a (meth)acryl equivalent of 250 to 3,000, which is a molecular weight per one (meth)acrylamide group, and is obtained by an addition reaction of an alcohol compound having one or more hydroxyl groups per molecule, wherein the alcohol compound has one or more kinds of an olefin skeleton, an isocyanate compound having two or more isocyanate groups per molecule, and an N-substituted (meth)acrylamide compound containing a hydroxyl group represented by formula [1]

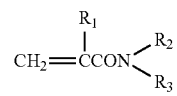

[1]

wherein $R_1$ represents a hydrogen atom or a methyl group, $R_2$ and $R_3$ may be the same or different from each other, $R_2$ and $R_3$ represent a hydrogen atom or a linear or branched alkyl group having 1 to 6 carbon atoms or an aliphatic ring or an aromatic ring having 3 to 6 carbon atoms, which may be substituted with a hydroxyl group, and wherein $R_2$ and $R_3$ may form, together with the nitrogen atom to which they are attached, a saturated or unsaturated 5- to 7-membered ring, in which 5- to 7-membered ring, an oxygen atom or a nitrogen atom other than the aforementioned nitrogen atom may be additionally contained, with the proviso that $R_2$ and $R_3$ are not both a hydrogen atom and $R_2$ and $R_3$ are not both an alkyl group and that $R_2$ and $R_3$ have one or more hydroxyl groups in total.

11. An active energy ray curable resin composition comprising 1 to 100% by weight of the urethane modified (meth)acrylamide compound (A) according to claim 10, 0 to 90% by weight of polyfunctional (meth)acryl compound (B), and 0 to 90% by weight of monofunctional (meth)acryl compound (C).

12. An active energy ray curable cohesive composition comprising the compound according to claim 10.

13. An active energy ray curable adhesive composition comprising the compound according to claim 10.

14. A urethane modified (meth)acrylamide compound which comprises one or more urethane bonds and one or more (meth)acrylamide groups in the molecule, wherein the urethane modified (meth)acrylamide compound has a number average molecular weight of 250 to 1,500 and a (meth)acryl equivalent of 250 to 750, which is a molecular weight per one (meth)acrylamide group, and is obtained by an addition reaction of an alcohol compound having one or more hydroxyl groups per molecule, wherein the alcohol compound has one or more kinds of an ether skeleton, an isocyanate compound having two or more isocyanate groups per molecule, and an N-substituted (meth)acrylamide compound containing a hydroxyl group represented by formula [1]

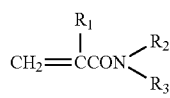

[1]

wherein $R_1$ represents a hydrogen atom or a methyl group, $R_2$ and $R_3$ may be the same or different from each other, $R_2$ and $R_3$ represent a hydrogen atom or a linear or branched alkyl group having 1 to 6 carbon atoms or an aliphatic ring or an aromatic ring having 3 to 6 carbon atoms, which may be substituted with a hydroxyl group, and wherein $R_2$ and $R_3$ may form, together with the nitrogen atom to which they are attached, a saturated or unsaturated 5- to 7-membered ring, in which 5- to 7-membered ring, an oxygen atom or a nitrogen atom other than the aforementioned nitrogen atom may be additionally contained, with the proviso that $R_2$ and $R_3$ are not both a hydrogen atom and $R_2$ and $R_3$ are not both an alkyl group and that $R_2$ and $R_3$ have one or more hydroxyl groups in total.

15. An active energy ray curable resin composition comprising 1 to 100% by weight of the urethane modified (meth)acrylamide compound (A) according to claim 14, 0 to 90% by weight of polyfunctional (meth)acryl compound (B), and 0 to 90% by weight of monofunctional (meth)acryl compound (C).

16. An active energy ray curable cohesive composition comprising the compound according to claim 14.

17. An active energy ray curable adhesive composition comprising the compound according to claim 14.

18. An active energy ray curable inkjet ink composition comprising the compound according to claim 14.

19. An active energy ray curable coating composition comprising the compound according to claim 14.

20. An active energy ray curable coating composition for finger nail decoration comprising the compound according to claim 14.

* * * * *